(12) United States Patent
Magda et al.

(10) Patent No.: US 9,818,191 B2
(45) Date of Patent: Nov. 14, 2017

(54) COVARIATE MODULATE ATLAS

(71) Applicant: CORTECHS LABS, INC., San Diego, CA (US)

(72) Inventors: Sebastian Magda, San Diego, CA (US); Christopher N. Airriess, San Diego, CA (US); Nathan S. White, San Diego, CA (US)

(73) Assignee: CorTechs Labs, Inc., San Diego, CA (US)

( * ) Notice: Subject to any disclaimer, the term of this patent is extended or adjusted under 35 U.S.C. 154(b) by 0 days.

(21) Appl. No.: 15/087,986

(22) Filed: Mar. 31, 2016

(65) Prior Publication Data

US 2016/0292859 A1  Oct. 6, 2016

Related U.S. Application Data

(60) Provisional application No. 62/140,903, filed on Mar. 31, 2015.

(51) Int. Cl.
| | |
|---|---|
| *G06T 7/00* | (2017.01) |
| *G06F 19/00* | (2011.01) |
| *G06T 7/11* | (2017.01) |
| *G06T 7/143* | (2017.01) |
| *G06T 7/33* | (2017.01) |

(52) U.S. Cl.
CPC .......... *G06T 7/0014* (2013.01); *G06F 19/321* (2013.01); *G06T 7/11* (2017.01); *G06T 7/143* (2017.01); *G06T 7/33* (2017.01); *G06T 2207/20081* (2013.01); *G06T 2207/20128* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 6,430,430 B1 * | 8/2002 | Gosche | G06T 7/0012 |
| | | | 128/920 |
| 7,324,842 B2 | 1/2008 | Dale et al. | |
| 8,140,144 B2 | 3/2012 | Dale et al. | |
| (Continued) | | | |

OTHER PUBLICATIONS

Bartsch et al. "A web-portal for interactive data exploration, visualization, and hypothesis testing," Frontiers in Neuroinformatics, Mar. 26, 2014; vol. 8, No. 25.*

(Continued)

*Primary Examiner* — Matthew Bella
*Assistant Examiner* — Soo Shin
(74) *Attorney, Agent, or Firm* — Pillsbury Winthrop Shaw Pittman LLP

(57) ABSTRACT

The disclosed technology relates generally to medical imaging, and more particularly, some embodiments relate to systems and methods for creating and using a covariate modulated or "dynamic" atlas. Some embodiments of the disclosure provide a method for predicting an alas using General Additive Model (GAM) parameters, wherein the GAM parameters are derived by registering (and optionally segmenting) a plurality of image data sets from a plurality of different subjects to an initial atlas estimate (e.g., a seed atlas), and analyzing the resulting registration, segmentation, and intensity parameters as correlated with input covariates.

18 Claims, 20 Drawing Sheets

(56) References Cited

U.S. PATENT DOCUMENTS

| | | | |
|---|---|---|---|
| 2004/0127799 A1* | 7/2004 | Sorensen | G06T 7/0012 |
| | | | 600/481 |
| 2004/0220750 A1 | 11/2004 | Hinds | |
| 2005/0262031 A1 | 11/2005 | Saidi | |
| 2010/0067761 A1 | 3/2010 | Jakobsson | |
| 2010/0128953 A1 | 5/2010 | Ostrovsky-Berman | |
| 2010/0131526 A1 | 5/2010 | Sun | |
| 2011/0160543 A1* | 6/2011 | Parsey | A61B 5/055 |
| | | | 600/300 |
| 2013/0060305 A1* | 3/2013 | Bokil | A61N 1/0529 |
| | | | 607/62 |
| 2013/0178733 A1 | 7/2013 | Langleben | |
| 2013/0223714 A1* | 8/2013 | Lipton | G06T 7/0012 |
| | | | 382/131 |
| 2013/0267842 A1 | 10/2013 | Scheuering | |
| 2014/0081660 A1 | 3/2014 | Hasanova | |
| 2014/0111508 A1 | 4/2014 | Bystrov | |
| 2015/0045651 A1* | 2/2015 | Crainiceanu | A61B 5/055 |
| | | | 600/410 |
| 2016/0210435 A1* | 7/2016 | Neumann | G06F 19/321 |

OTHER PUBLICATIONS

Serag et al.; Construction of a consistent high-definition spatio-temporal atlas of the developing brain using adaptive kernel regression; NeuroImage; vol. 59; pp. 2255-2265; (2012).

Murgasova, et al.; "Construction of a Dynamic 4D Probabilistic Atlas for the Developing Brain;" Proc. Intl. Mag. Reson. Med., vol. 18; p. 4381; (2010).

Hill, et al; "A Dynamic Brain Atlas;" University of Oxford; vol. 2488; pp. 532-539; (2002).

Habas et al.; "A spatiotemporal atlas of MR intensity, tissue probability and shape of the fetal brain with application to segmentation;" Neuroimage; vol. 53; No. 2; pp. 460-470; (2010).

Ericsson et al.; "Construction of a Patient-Specific Atlas of the Brain: Application to Normal Aging;" ISBI; pp. 480-484; (2008).

Murgasova et al.; "A Dynamic 4D Probabilistic Atlas of the Developing Brain;" Neuroimage; vol. 54; pp. 2750-2763; (2011).

Davis et al.; "Population Shape Regression From Random Design Data;" 11th IEEE International Conference on Computer Vision; 7 pages; (2007).

PCT Application No. PCT/US2016/025406 International Search Report and Written Opinion dated Jun. 30, 2016. (12 pages).

* cited by examiner

| SUBJECT | 1 | 2 | 3 |
|---|---|---|---|
| INTENSITY | 100 | 200 | 50 |
| TISSUE TYPE | 1 | 1 | 2 |

Figure 15A

| STEP | STEP 1 | STEP 2 | STEP 3 | |
|---|---|---|---|---|
| TISSUE TYPE | 1 | 1 | 1 | 2 |
| MEAN | 100 | 150 | 150 | 50 |
| VARIANCE | 0 | 50 | 50 | 0 |
| PROBABILITY | 1 | 1 | 2/3 | 1/3 |

Figure 15B

COVARIATE MODULATE ATLAS

TECHNICAL FIELD

The disclosed technology relates generally to medical imaging, and more particularly, some embodiments relate to systems and methods for creating and using a covariate modulated or "dynamic" atlas.

BACKGROUND

Anatomical segmentation generally refers to the delineation of anatomical structures apparent in medical imaging data. For example, segmentation may be applied by software to medical resonance imaging (MRI) data of a human brain to delineate neuroanatomical structures using boundaries defined by contrast variations within an image set. The same concept may be applied to imaging data from other imaging modalities such as computed tomography (CT), positron emission tomography (PET), or other medical imaging modalities, and applied to other organs, such as the heart, liver, kidneys, or lungs. The segmentation process may be automated through the use of computer software to automatically identify anatomical boundaries. Anatomical segmentation may rely on a number of image features, including signal intensity, global as well as local position with relation to neighboring structures, texture, and shape. Joint information from several different imaging techniques is often combined to provide additional information.

Moreover, segmentation may be used automatically identify specific anatomical features within segment boundaries. Automated segmentation labeling may be useful for efficiently and reliably identifying abnormalities. For example, such abnormalities may be relevant to identifying and/or diagnosing disease and/or pathologies that may affect patient care.

Generally, automated segmentation labeling algorithms rely on registering imaging data to an atlas. The atlas, for example, may be a predefined map of the target organ, such as a brain, heart, kidney, liver, lungs, or other organs, as well as information about the expected characteristics about the target organ. However, anatomic variations among a target population may impede accurate anatomical segmentation that relies on a single reference atlas. For example, morphometric differences may be associated with natural genetic differences, age, gender, ethnicity, and various diseases.

Automatic segmentation techniques may distinguish common underlying anatomical structure present in most organisms. There is often an expected identifiable local and sometimes global arrangement of tissues that can be grouped into structures, or organs. For example, techniques may take advantage of global structure by using landmark locations of easily identifiable locations as the starting point, including graph cuts, machine learning, Bayesian classification, or level sets. Atlas-based segmentation techniques may use global statistical information to distinguish anatomical variations, as opposed to relying on landmarks. Segmentation may then include fitting of the image data to a statistical atlas and classifying the fitted data set in the atlas space.

BRIEF SUMMARY OF EMBODIMENTS

According to various embodiments of the disclosed technology, a method for creating a covariate modulate atlas includes receiving a plurality of subject dependent image data sets from an image data source and, for each subject dependent image data set, receiving one or more covariates from the image data source, demographic data source, or user input, and one or more atlas parameters. Creating and using a covariate modulated atlas, consistent with embodiments disclosed herein, enables efficient and uniform segmentation of anatomical structures by providing continuity of atlas data for a complete and discrete set of covariates. For example, covariates may include demographic parameters such as age, gender, ethnicity, genetic factors, medical history and/or relevant clinical measures. Covariates may also include user input parameters which may be treated as an extension of demographic parameters and may include parameters such as diagnosis, medical history data, reason for exam, clinical measures, clinical history, manual input to compensate for any missing and/or incorrect parameters, and/or other parameters. Covariates may also include imaging modality parameters (for example scanner type, field strength, flip angle, acquisition properties such as TR, TE for MR modality), various manufacturer's software or hardware specifications. Atlas parameters may be part of the initial or seed atlas, and include anatomic structure statistical parameters such as mean local signal intensity in different modalities including but not limited to magnetic properties such as T1, T2, proton density (PD), magnetization transfer, diffusion tensor and derived variables for MR modality and prior probabilities for local and neighboring anatomical structures or tissues, as well as anatomical structure's local shape and texture. These lists of covariate and atlas parameters are for exemplary purposes, and one of skill in the art would appreciate that any other demographic, user input, or imaging modality parameter may be used.

The method may include, for a first subject, registering a first subject dependent image data set to an atlas estimate and returning a first set of registration parameters. For example, each registration parameter may be rigid body, affine, or nonlinear registration parameters and may indicate how each image data point (e.g., each voxel) is transformed during registration, such that a set of registration parameters describes how the subject dependent image data set is transformed through registration to the atlas estimate. The method may also include receiving one or more subject dependent intensity parameters transformations to voxel intensity (e.g., contrast and/or brightness) during the registration process based on image modality parameters, manufacturer's software and hardware specifications. In some embodiments, the method also includes segmenting the subject dependent image data based on the atlas estimate and returning a first set of segmentation parameters.

The General Additive Model (GAM) server may then use a GAM engine to process the registration parameters, segmentation parameters, and/or intensity parameters to calculate a set of GAM parameters that can be applied to the first set of subject dependent covariates to generate a subject dependent atlas estimate. The GAM parameters and corresponding covariates and atlas parameters may then be stored in a data store, and the process may be repeated for additional subjects.

For example, the method may also include receiving, for a second subject, a second subject dependent image data set and corresponding covariates and atlas parameters, registering (and segmenting) the second subject dependent image data to the atlas estimate, and receiving a second set of registration parameters, intensity parameters, and/or segmentation parameters. These second sets of registration parameters, intensity parameters, and/or segmentation parameters may then be used by the GAM engine to calculate a second set of GAM parameters corresponding to the second set of covariates and storing the GAM parameters with the corresponding covariates and atlas parameters. This cycle may repeat for multiple additional subjects. Some embodiments may include, for each subject, evaluating the quality of fit of each subject dependent image set to the atlas estimate, and discarding the data set if the quality of fit falls below a threshold value.

The method may also include, for any subject, calculating with the prediction engine in the GAM server an updated atlas estimate as a function of the subject dependent GAM parameters as applied to the subject dependent covariates, and also incorporating the corresponding atlas parameters. The subject dependent image data set may then be registered and segmented on the updated atlas estimate, returning registration parameters, segmentation parameters, and intensity. The GAM server may then evaluate the quality of registration, and this process may repeat until convergence is reached.

Some embodiments of the disclosed technology provide a method for applying a covariate modulate atlas. The method for applying a covariate modulate atlas may include receiving a target image data set from an imaging data source and receiving target covariates from a demographic data source, imaging data source, and user input. In some embodiments, "target" may be substantially synonymous with "subject". In some embodiments, "target" may refer to an organ, or other body parts and/or regions of a "subject". As such, a target image data set may be an image data set of a target region for a particular subject. The target region may be an organ such as a brain, a heart, a liver, a kidney, or any other anatomical structure of interest. The target subject may be a human, or other animal species. The target image data set, then, is the image data set that is intended for segmentation and labeling. For example, a target could be a 59 year old male with memory issues. Then the target data set could be an MR image set and target covariates could be demographic: age (59 yo), gender (male), visit reason (memory issues) and imaging modality parameters: modality (MR), scanner model, etc. The method may also include using the prediction engine to calculate a covariate modulate atlas prediction by applying the stored GAM parameters and atlas parameters to the target covariates. The method may also include registering the image data set to the covariate modulate atlas prediction. In some embodiments, the method may also include segmenting the image data set using the covariate modulate atlas prediction.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIGS. 15A and 15B illustrate sample data for determination of the content of a node of an atlas.

Figure 1:
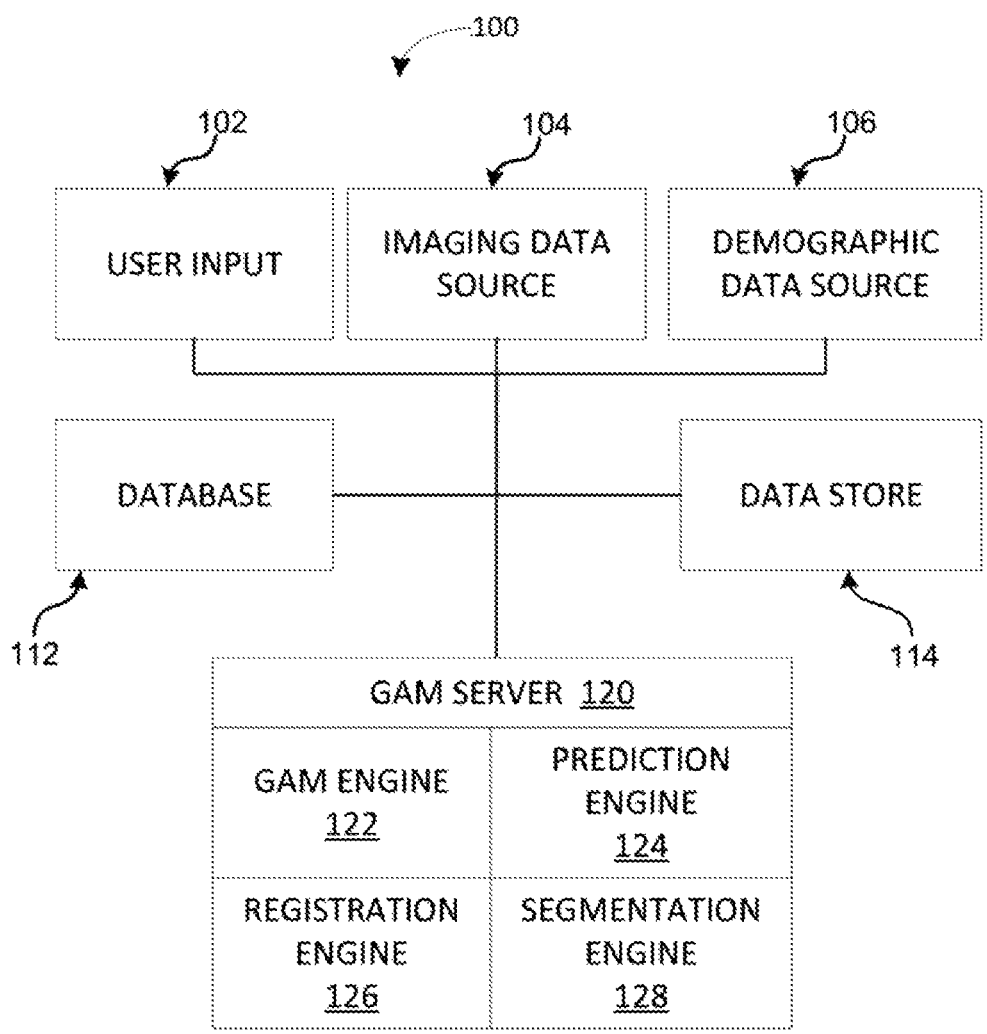
FIG. 1 is a block diagram that illustrates a system for creating and using a covariate modulate atlas, consistent with embodiments disclosed herein.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The technology disclosed herein is directed toward a system and method for creating and using a dynamic atlas. Some embodiments of the disclosure provide a method for predicting an alas using General Additive Model (GAM) parameters, wherein the GAM parameters are derived by registering (and optionally segmenting) a plurality of image data sets from a plurality of different subjects to an initial atlas estimate (e.g., a seed atlas), and analyzing the resulting registration, segmentation, and intensity parameters as correlated with input covariates.

Atlas-based segmentation techniques that use static atlas, do not efficiently distinguish anatomic variation within a population from spatial tissue arrangements within a target image set. In the process of fitting a mapping function is constructed from the image space to the atlas space. In general, the ability of a system to create an accurate mapping into the atlas space allows for better tissue segmentation by reducing the variability within the atlas necessary to capture all anatomical variations. Mapping techniques may involve applying scaling transformations and some form of a non-linear deformation of a static atlas data set to a target image data set. The mapping technique may be applied globally or locally on particular regions or structures of interest (ROI). For example, registration may include using a probabilistic mesh-based method, machine learning, or other atlas-based registration techniques known in the art.

Another approach may incorporate an atlas that models a specific population subgroup. Individuals in a population may be grouped based on general anatomical similarity, or based on specific demographic factors that potentially affect anatomy in a similar way, such as age, gender, ethnicity, genetics, or diseases. Reducing the population scope automatically decreases the anatomical variability that needs to be represented in a single atlas. A set of atlases may then be constructed, one for each subgroup. Anatomical segmentation may be accomplished by selecting an appropriate atlas from the multi-atlas set based either on demographics or on the best similarity measure after alignment of the atlas with the target image data set. The final segmentation may also be computed by merging segmentations generated from multiple atlases based on statistical, or voting strategies, or by using a weighting of atlases that provide the best similarity measure.

Creating and using a covariate modulated atlas, consistent with embodiments disclosed herein, enables efficient and uniform segmentation of anatomical structures by providing continuity of atlas data for a complete and discrete set of covariates. For example, covariates may include demographic parameters, imaging data parameters, user input, and/or other covariates. Imaging data parameters may include without limitation: imaging modality parameters (for example scanner type, field strength, flip angle, acquisition properties such as TR, TE for MR modality). Demographic parameters may include without limitation: age, gender, ethnicity, genetic factors, medical history, relevant clinical measures, and/or other parameters. User input can be treated as an extension of demographic parameters and may include without limitation: diagnosis, medical history data, reason for exam, clinical measures, manual input to compensate for any missing or incorrect parameters, and/or other parameters. In some embodiments, atlas parameters may include anatomic structure statistical parameters such as mean local signal intensity in different modalities including but not limited to magnetic properties such as T1, T2, proton density (PD), magnetization transfer, diffusion tensor and derived variables for MR modality and prior probabilities for local and neighboring anatomical structures or tissues, as well as anatomical structure's local shape and texture.

FIG. 1 is a block diagram that illustrates a system for creating and using a dynamic atlas. As illustrated, a system for building and using a covariate modulate atlas 100 may include data sources such as a user input data source 102, an imaging data source 104, and a demographic data source 106. Imaging data source 104 may include imaging modalities such as an MRI system, a CT system, a PET system, an Ultrasound (US) system, and X-Ray system, or other imaging modalities as known in the art. Imaging data source 104 may also include image archive data sources, such as a Picture Archive Communication System (PACS), a Vendor Neutral Archive (VNA), or any other image archive system capable of storing and transmitting image data sets, such as, without limitation, DICOM format data sets.

In some examples, imaging data source 104 may also provide demographic data, as part of a DICOM data set that includes both imaging data and corresponding demographic data. In addition, demographic data source 106 may include demographic information database systems such as hospital information systems (HIS), radiology information systems (RIS), electronic medical records (EMR), electronic health systems (EHS), or other demographic data systems as known in the art.

User input data source 102 may include a computer terminal (e.g., a workstation with a keyboard and monitor), a handheld computer, smartphone, tablet computer, laptop, or any other user input device as known in the art. User input data source 102, imaging data source 104, and demographic data source 106 may each provide covariates to GAM server 120. Each of user input data source 102, imaging data source 104, and demographic data source 106 may transmit and save data in database 112, stored on data store 114.

GAM server 120 may communicate with database 112 and data store 114. For example, GAM server 120 may receive an atlas estimate or seed atlas data set from database 112, or directly from imaging data source 104. For example, the imaging data source 104 may be any of the imaging modalities and/or PACS system, as described above. Embodiments of the covariate modulate atlas building process disclosed herein do not depend on a particular seed atlas data set, but can operate off of any imaging data set that provides an initial atlas estimate.

GAM server 120 may operate on one or more computer processors and memory, consistent with computer hardware embodiments disclosed herein. GAM server 120 and may also include GAM engine 122, prediction engine 124, registration engine 126, and segmentation engine 128. For example, GAM engine 122 may receive covariates from imaging data source 104, demographic data source 106, user input 102, or data store 114, and calculate GAM parameters as a function of registration parameters, segmentation parameters, and/or intensity parameters returned following registration of an image data set to an atlas estimate (e.g., the seed atlas). The GAM parameters may then be stored with the covariates and atlas parameters in a data store, and subsequently retrieved, along with the atlas parameters, and applied to a target set of covariates to create an atlas prediction.

As disclosed herein, the GAM engine, prediction engine, registration engine, and segmentation engine may each be computer modules programmed for the specialized purposes of calculating GAM functions, calculating atlas predictions based on GAM parameters, registering an image data set to an atlas, and segmenting an image data set to an atlas, respectively, consistent with methods disclosed herein. For example, an engine may be a computer processor. The computer processor may include a non-transitory computer readable media with software programmed thereon, the software configured to perform either GAM functions, prediction functions, registration functions, or segmentation functions, consistent with methods disclosed herein, depending on the type of engine described.

A target image data set may be an image data set of a target region for a particular subject, received from imaging data source 104. As described above, the target region may be an organ such as a brain, a heart, a liver, a kidney, or any other anatomical structure of interest. The target subject may be a human, or other animal species. The target image data set, then, is the image data set that is intended for segmentation and labeling.

Still referring to FIG. 1, registration engine 126 may receive the an atlas estimate from GAM engine 122 and the target image data set from either imaging data source 104 or database 112. For example, the GAM engine may send covariates, atlas data, and a seed atlas to registration engine 126, and receive registration parameters from registration engine 126. In some embodiments, registration engine 126 receives an imaging data set from imaging data source 104 and registers the imaging data set to an atlas estimate or seed atlas, according to registration methods disclosed herein. Registration engine 126 may then register the target image data set to the atlas estimate using an atlas registration process. For example, the atlas registration process may be a manual registration wherein a user matches atlas estimate boundary structures with the target image data set boundary structures. Alternatively, various automated atlas registration processes may be used, consistent with embodiments disclosed herein.

For any subject and target image data set, GAM engine 122 may receive registration parameters and/or intensity parameters from the registration engine 126, correlate with subject dependent covariates, and calculate GAM parameters. In some embodiments, the GAM engine 122 may calculate a quality of fit resulting from the registration of the subject dependent image data set to the atlas estimate. For example, the quality of fit may be the result of a cost function comparing the image data set to the atlas estimate. If the quality of fit falls below a predetermined threshold, the registration parameters may be discarded. If the quality of fit falls within the threshold range, then the GAM engine may use the registration parameters, segmentation parameters, and/or intensity parameters to calculate GAM parameters, and may store the GAM parameters with the atlas parameters, in data store 114. In some embodiments, segmentation engine 128 may segment the image data and return a segmentation data set to GAM engine 122. If the quality of fit falls above the desired threshold, GAM engine 122 may store the segmentation data set along with the subject dependent GAM parameters and the registration parameters. The steps described above may be repeated for multiple image data sets across multiple subjects, such that GAM engine 122 may calculate, update, and store GAM parameter data sets for a plurality of subjects.

In some embodiments, prediction engine 124 may calculate an updated atlas estimate according to subject dependent covariates as applied to stored atlas parameters and GAM parameters. The GAM server 120 may then receive and register the corresponding subject dependent image data set to the updated atlas estimate, receive new registration, intensity, and or segmentation parameters, and re-calculate and/or update the GAM parameters. This process may repeat iteratively until convergence is achieved.

Figure 2A:
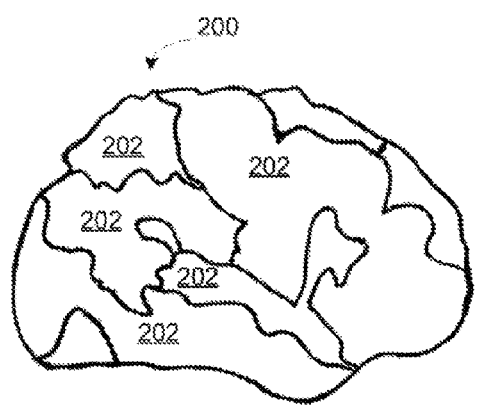
FIG. 2A illustrates an example of an anatomical atlas of a brain.
Figure 2B:
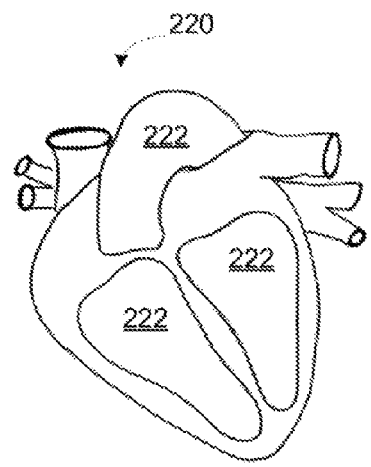
FIG. 2B illustrates an example of an anatomical atlas of a heart.
Figure 2C:
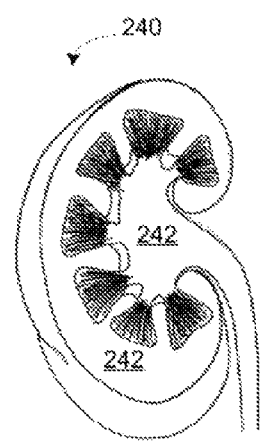
FIG. 2C illustrates an example of an anatomical atlas of a kidney.
Figure 2D:
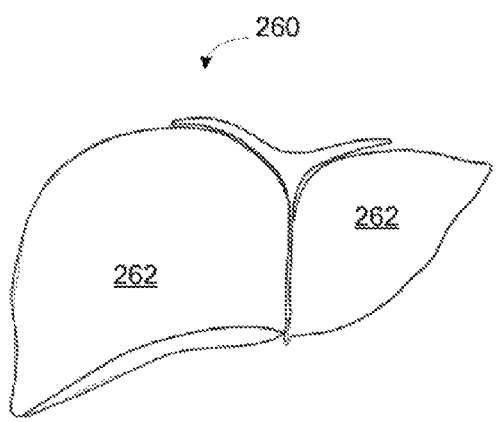
FIG. 2D illustrates an example of an anatomical atlas of a liver.

FIGS. 2A-2D illustrate example anatomical atlases, as may be used by embodiments of the present disclosure. In particular, FIG. 2A illustrates an example atlas of a human brain. FIG. 2B illustrates an example atlas of a heart. FIG. 2C illustrates an example atlas of a kidney. And, example 2D illustrates an example atlas of a liver. However, it should be understood that embodiments of the present disclosure may use anatomical atlases for other target regions in the human body, or in other species. For example, anatomical atlases may include any other anatomical structure, and may represent anatomies consistent with humans, dogs, cows, horses, or any other animal species.

As illustrated, an atlas of the brain 200 may be pre-segmented into various regions of interest (ROI) 202. The atlas of the heart 220 may be pre-segmented into various segments 222. The atlas of the kidney 240 may be pre-segmented into various segments 242. And the atlas of the liver may be pre-segmented into various segments 262. Boundary lines drawn between those ROI's that may be matched with boundary lines defined by contrast variations within the target image data set. The segmented ROIs 202, 222, 242, and 262 are non-limiting, and one of skill in the art would appreciate that there may be more or fewer ROIs depending on the desired level of segmentation, the field of view and cross-sectional perspective of the target image, and the selection of anatomical region and species. Moreover, for ease of explanation of many of the embodiments disclosed herein, the example atlases 200, 220, 240, and 260 are single 2-dimensional slices. However, one of skill in the art would appreciate that the atlas may include multiple image slices in different imaging planes, such that the image slices may be reconstructed to represent a 3-dimensional atlas.

Figures 3A, 3B:
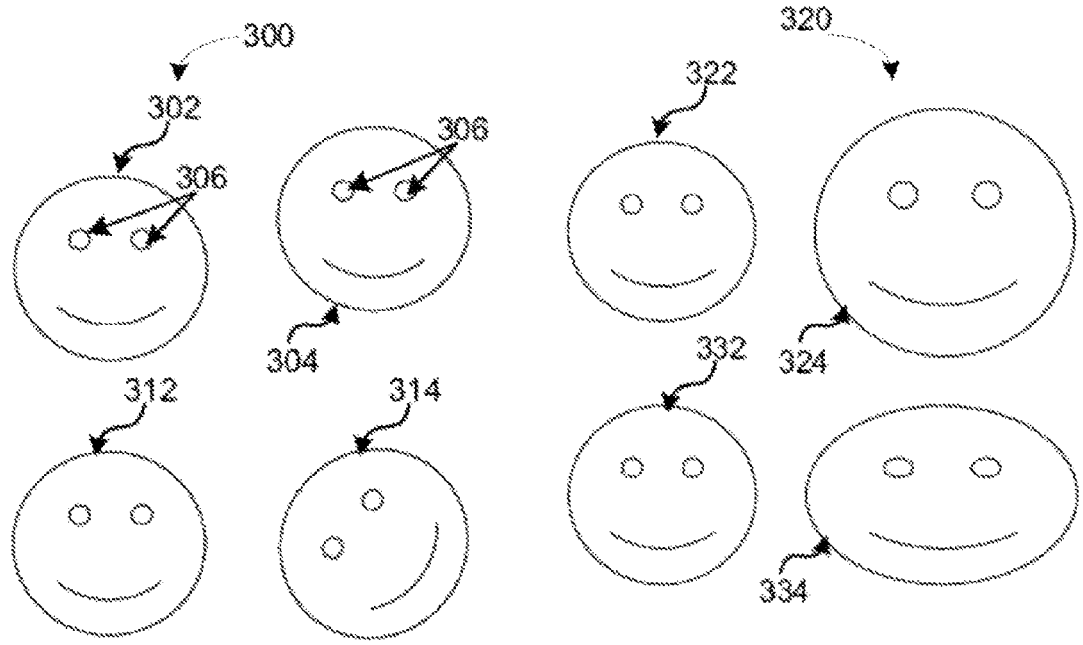
FIG. 3A is a diagram illustrating an example rigid body atlas registration.
FIG. 3B is a diagram illustrating an example affine atlas registration.

FIG. 3A is a diagram illustrating an example rigid body atlas registration. Referring back to FIG. 1, and still to FIG. 3A, registration engine 126 may employ various registration processes. For example, registration engine 126 may employ a rigid body atlas registration process 300 to register the image data set to the atlas estimate data set. Rigid body registration process 300 may include translating a first image 302 to align with a second image 304 by translating the first image in an x-axis (i.e., a horizontal axis), a y-axis (i.e., a vertical axis perpendicular to y-axis), or a z-axis (i.e., an axis perpendicular to both the x-axis and the y-axis). For example, the first image may be the image data set and the second image may be the atlas estimate data set. Alternatively, the first image may be the atlas estimate data set and the second image may be the image data set. In addition, first image 312 may be rotated to align with second image 314. A single rigid body registration may include both translation and rotation. In some examples, registration engine 122 may use fiducial points 306 to assist in the registration process. For example, fiducial points 306 may be implanted fiducial markers that have a high contrast profile relative to the specific imaging modality being used to capture the image data. Alternatively, fiducial points 320 may be recognizable anatomical features.

For example, rigid body registration process 300 may start with a series of rigid body registration processes 300 in varying degrees of movement to bring a first image in closer and closer registrative correlation with a second image. Each of the rigid body translations applied will position the first image into a new orientation with respect to the second image, and at each orientation, a cost function, c, may be evaluated:

$$c(\alpha_1, \ldots, \alpha_n) = \frac{1}{N}\sum_{i=1}^{N} m_i[S(L(\vec{\alpha})\cdot\vec{r}_i) - T(\vec{r}_i)]^2 \quad (1)$$

Referring to Equation 1, N represents the number of voxels in the first image, $r_i$ is the location of the center of a given voxel i in the first image, and the first image has an image intensity represented by $S(r_i)$ and the second image has an image intensity represented by $T(r_i)$. $\alpha_1, \ldots, \alpha_n$ represent translation and rotation parameters, and in the example of a covariate modulate atlas, may represent GAM parameters. $L(\alpha)$ represents a current estimate of the rigid body transformation operator which acts on spatial coordinates of voxels in S, and $m_i$ represents a target image mask value for voxel i. Accordingly, the cost function value may represent the quality of the registration of the first image to the second image. Thus, for any choice of $\alpha$, if L reduces the cost c, the quality of the registration has improved. The translation and rotation process may be applied iteratively until the c stops decreasing.

As illustrated in FIG. 3B, a registration process 306 may also correct for zoom or shear. For example, registration engine 126 may employ an affine registration. An affine registration transforms a first image in a first image space into a second image in a second image space using an affine function that preserves pointes, straight lines, and planes, while allowing angles between lines or distances between points to change. An affine registration process may include translation, scaling, homothety, similarity transformation, reflection, rotation, shear mapping, combinations of any of these transformations, or other affine registration techniques as known in the art. Thus, rigid body registration process 300 may actually be thought of as a subset of affine registration process 320. An affine transformation incorporates a linear transformation of a first image space, X, to second images space, Y=Mx+b, where M represents a linear transformation. Accordingly, a first image 322 in the first image space X may be affine translated to register with a second image 324 in zoomed image space Y. Alternatively, a first image 332 in first image space X may be affine translated to register with a second image 334 in second sheared image space Y. The same cost function reduction approach applied in rigid body registration process 300 may be applied to affine registration process 320, but may incorporate the affine transformation of first image space X to second image space Y, affine specific cost function $f$ will decrease as the quality of the registration between first image 322 or 332 (represented as source image S) and second image 324 or 334 (represented as target image T) improves.

Figure 3C:
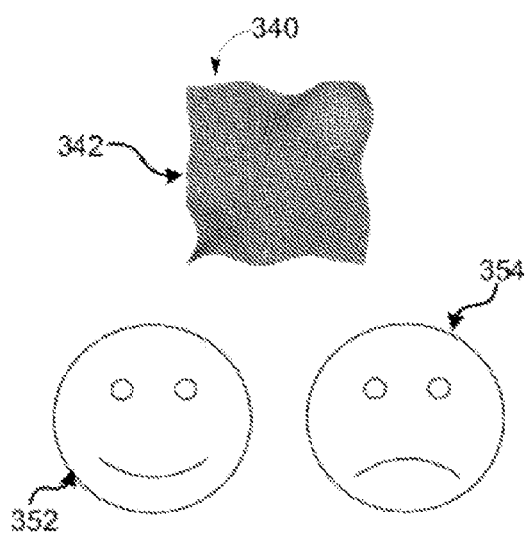
FIG. 3C is a diagram illustrating an example nonlinear or warping atlas registration.

As illustrated in FIG. 3C, the registration engine may also employ an example nonlinear or warping atlas registration 340. For example, the first image space, with first image 352, may be warped into the second image space, with second image 354. Any of these registration methods disclosed above may substitute any cost function analysis for Equation 1, as would be known in the art. Moreover, other image registration techniques may be used as known in the art. Any of these registration processes, or other known registration processes may be employed by registration engine 126.

Figure 4A:
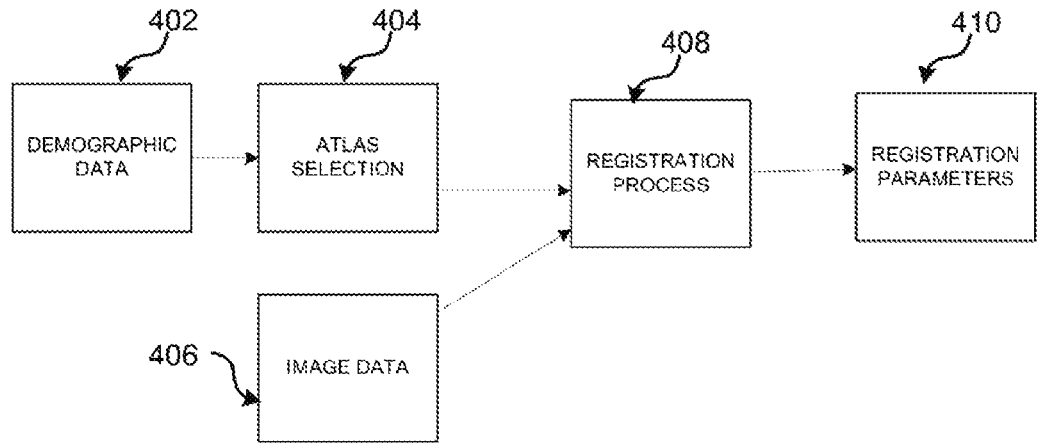
FIG. 4A is a block diagram that illustrates an example static atlas registration process.

FIG. 4A is a block diagram that illustrates an example atlas registration process. As illustrated, demographic data 402 may be used by the registration engine for atlas selection 404. For example, an atlas may be selected to correspond to a subject's age and gender. The atlas may be selected from a library of stored atlases (e.g., the library of stored atlases may be maintained in database 112, as illustrated in FIG. 1). Once the atlas is selected, the registration engine may use the atlas as a target image data set. The registration engine may then use image data 406, received from an image data source (e.g., the image data source 104 in FIG. 1), as a source image data set. The registration engine may then apply a registration process to register the source image data set to the target image data set. For example, the registration engine may employ a rigid body registration process, an affine registration process, a warping registration process, or a combination of any of these registration processes to register the source image data set to the target image data set.

Figure 4B:
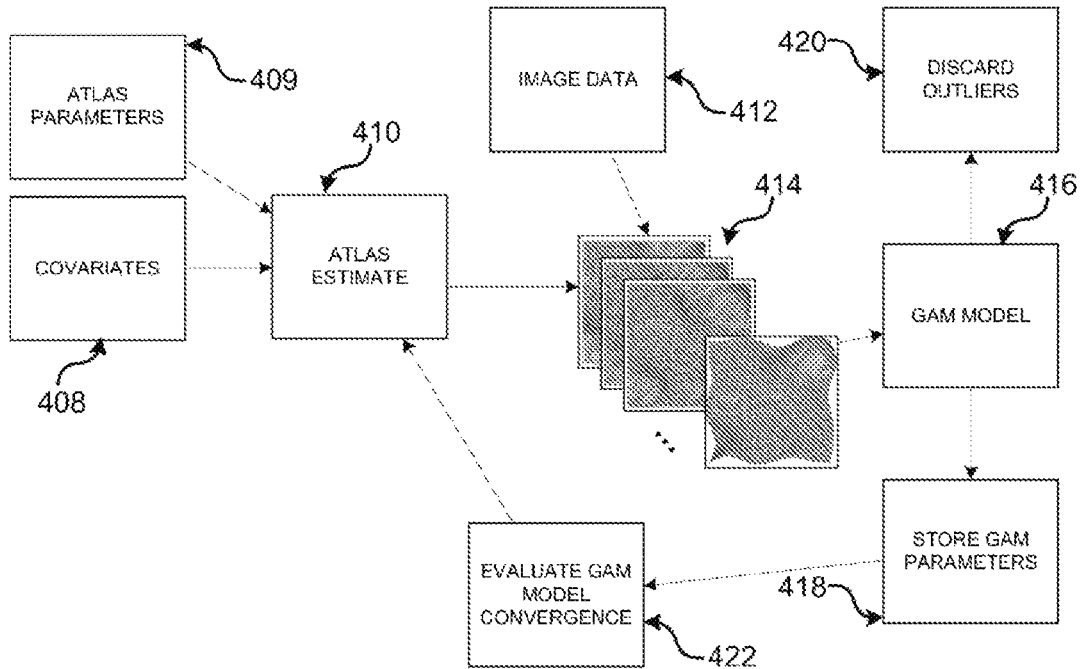
FIG. 4B is a block diagram that illustrates an example covariate modulate atlas building process, consistent with embodiments disclosed herein.

FIG. 4B is a diagram that illustrates example covariate modulate atlas creation process. Referring back to FIG. 1, and still to FIG. 4B, GAM server 120 may receive covariates 408, atlas parameters 409, initial atlas estimate 410 (e.g., a seed data set), and image data 412. Covariates 408 may include demographic parameters, imaging data parameters, and/or user input. Imaging data parameters may include without limitation: mean signal strength from different imaging modalities, imaging modality parameters (for example scanner type, field strength, flip angle, acquisition properties such as TR, TE for MR modality) width, center, brightness, contrast, gamma, signal to noise ratio, field of view, plane of view for 2-D image sets (axial, coronal, sagittal), table position, target anatomy, image sequence type (T1, T2, etc.), or other image parameters that may affect the appearance of an image data set for a given anatomical structure. Demographic parameters may include without limitation: age, gender, ethnicity, genetic factors, medical history, and/or relevant clinical measures. User input can be treated as an extension of demographic parameters and may include without limitation: diagnosis, medical history data, reason for exam, clinical measures, and/or manual input to compensate for any missing or incorrect parameters.

GAM server 120 may register image data 412 to atlas estimate 410 using registration engine 126, and return registration parameters. GAM server 120 may then evaluate the quality of fit of the image data to the atlas estimate (e.g., using cost function analysis), and discard outlier data 420 if the quality of fit falls below a pre-determined threshold. Alternatively, if the quality of fit meets or exceeds the threshold, then GAM engine 120 may store the registration parameters, as correlated with the subject dependent covariates 408. GAM server 120 may then calculate and store GAM parameters as a function of the registration parameters and subject dependent covariates at 418. The GAM server may repeat this process for multiple subjects and image sets to generate a complete set of GAM parameters.

GAM server 120 may also evaluate GAM convergence at 422 by registering image data 412 with an updated atlas estimate 410 by using prediction engine 124 to apply the GAM parameters and atlas parameters to the subject or target dependent covariates and re-registering the subject dependent image data set. This process may repeat iteratively until convergence is reached (e.g., the quality of fit between the image data and covariate modulate atlas falls within a pre-determined threshold value).

Figure 4C:
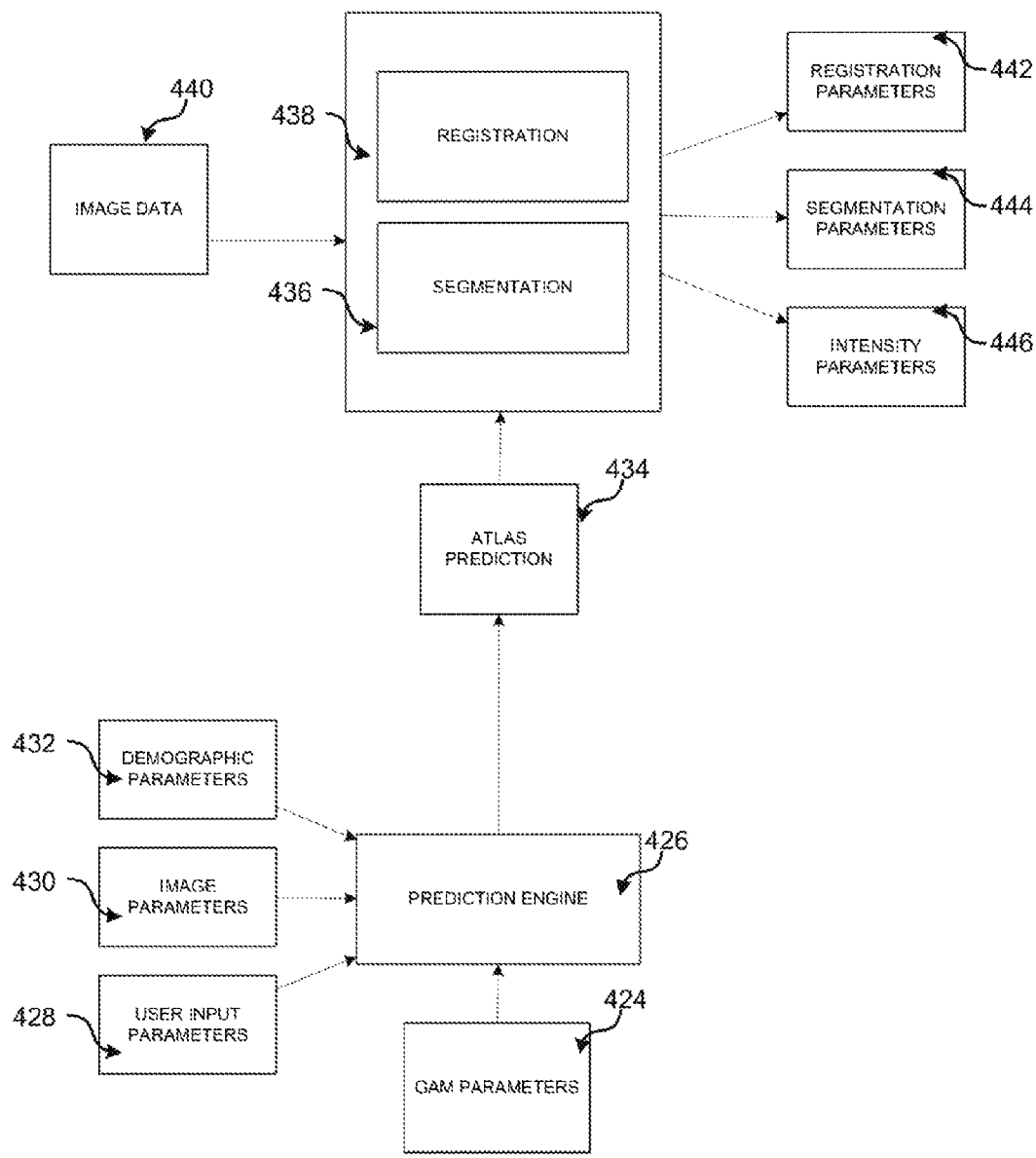
FIG. 4C is a block diagram that illustrates an example covariate modulate atlas creation process, consistent with embodiments disclosed herein.

FIG. 4C is a block diagram that illustrates an example covariate modulate atlas registration and segmentation process. For example, GAM server 120 may receive GAM parameters 424. GAM server 120, and in particular, prediction engine 124, may apply GAM parameter 424 to covariates 428, 430, and 432 to predict, at 426, atlas parameters as part of an atlas prediction. Registration engine 126 and segmentation engine 128 may then register and segment target image data 440 to the atlas prediction 434 and output registration parameters 442, segmentation parameters 444, and/or intensity parameters 446. For example, registration may utilize any of the registration processes described with respect to FIGS. 3A, 3B, and 3C, or any other registration process known in the art.

In some embodiments, the segmentation engine 128 may receive the image data 440 and segment the image data at 436. For example, segmentation may be performed by using known segmentation techniques and the available atlas parameters from the atlas prediction 434.

Figure 4D:
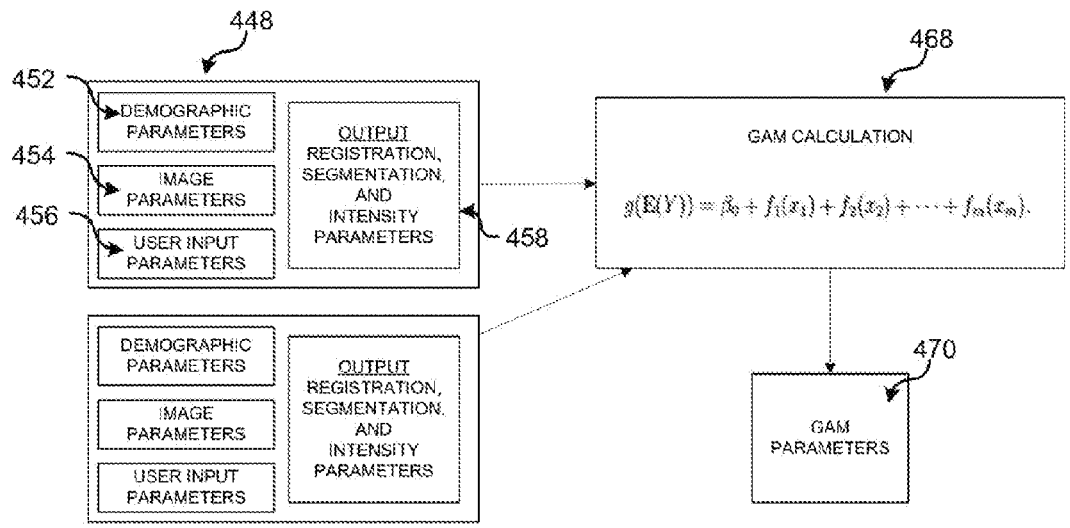
FIG. 4D is a block diagram that illustrates an example covariate modulate atlas creation process, consistent with embodiments disclosed herein.

FIG. 4D is a block diagram that illustrates an example covariate modulate atlas building process. GAM server 120 may receive covariates 452 (demographic parameters), 454 (image parameters), and 456 (user input parameters) for a first subject 448. The subject dependent image data may then be registered, and optionally segmented to an initial atlas estimate and registration, segmentation, and or intensity parameters are returned at 458. GAM engine 122 may then calculate GAM parameters to relate the subject dependent covariates 452, 454, and 456 to the registration, segmentation, and/or intensity output parameters using the GAM model. For example, the GAM model may fit Equation 2 below:

$$g(E(Y)) = \beta_0 + f_1(x_1) + f_2(x_2) + \ldots + f_m(x_m) \quad (2)$$

As illustrated by Equation 2, the covariate modulate atlas $g(E(Y))$ may incorporate a large set of GAM parameters, wherein each GAM parameter $f(x)$, at 470 in FIG. 4D, relates a specific covariate x to an estimated effect on the covariate modulate atlas. Accordingly, once a complete set of GAM parameters $f(x)$ are calculated, which may require a large enough set of subjects, then an atlas prediction can be made given any set of covariates.

Figure 4E:
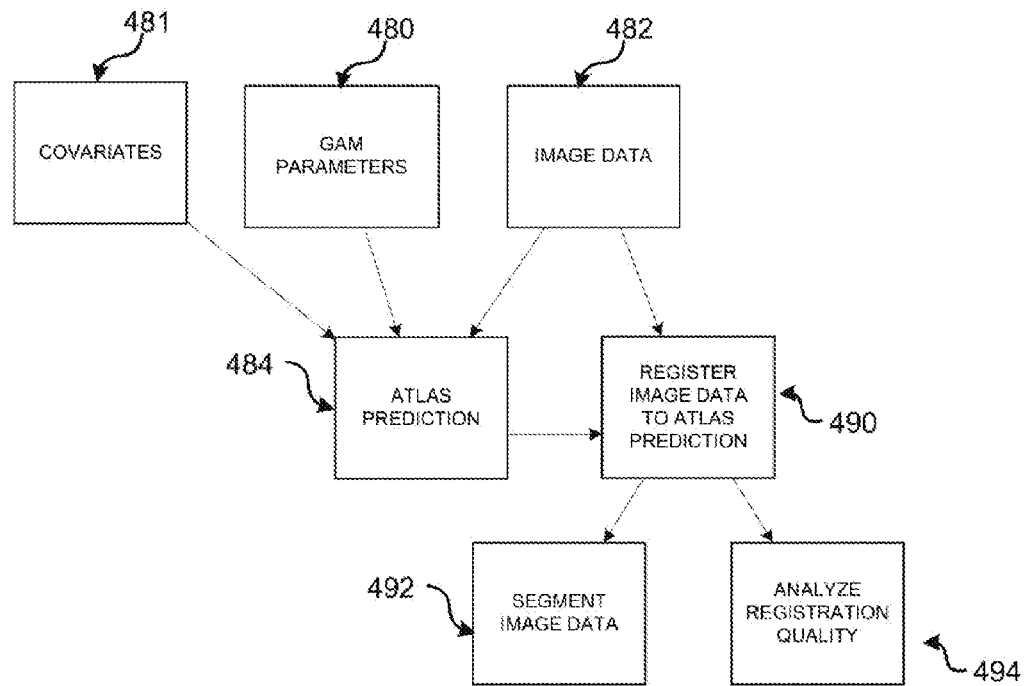
FIG. 4E is a block diagram that illustrates an example covariate modulate atlas application process, consistent with embodiments disclosed herein.

FIG. 4E is a block diagram that illustrates an example covariate modulate atlas application process. For example, GAM server 120 may receive GAM parameters 480 and covariates 481 corresponding to image data 482. GAM server 120 may use GAM parameter 480 and covariates 481 to predict an atlas estimate, for example, according to Equation 2. GAM server 120 may then register image data 482 to atlas prediction 484. GAM server 120 may also segment image data 482. GAM server 120 may also analyze the registration quality (e.g., using cost function analysis).

Figure 5:
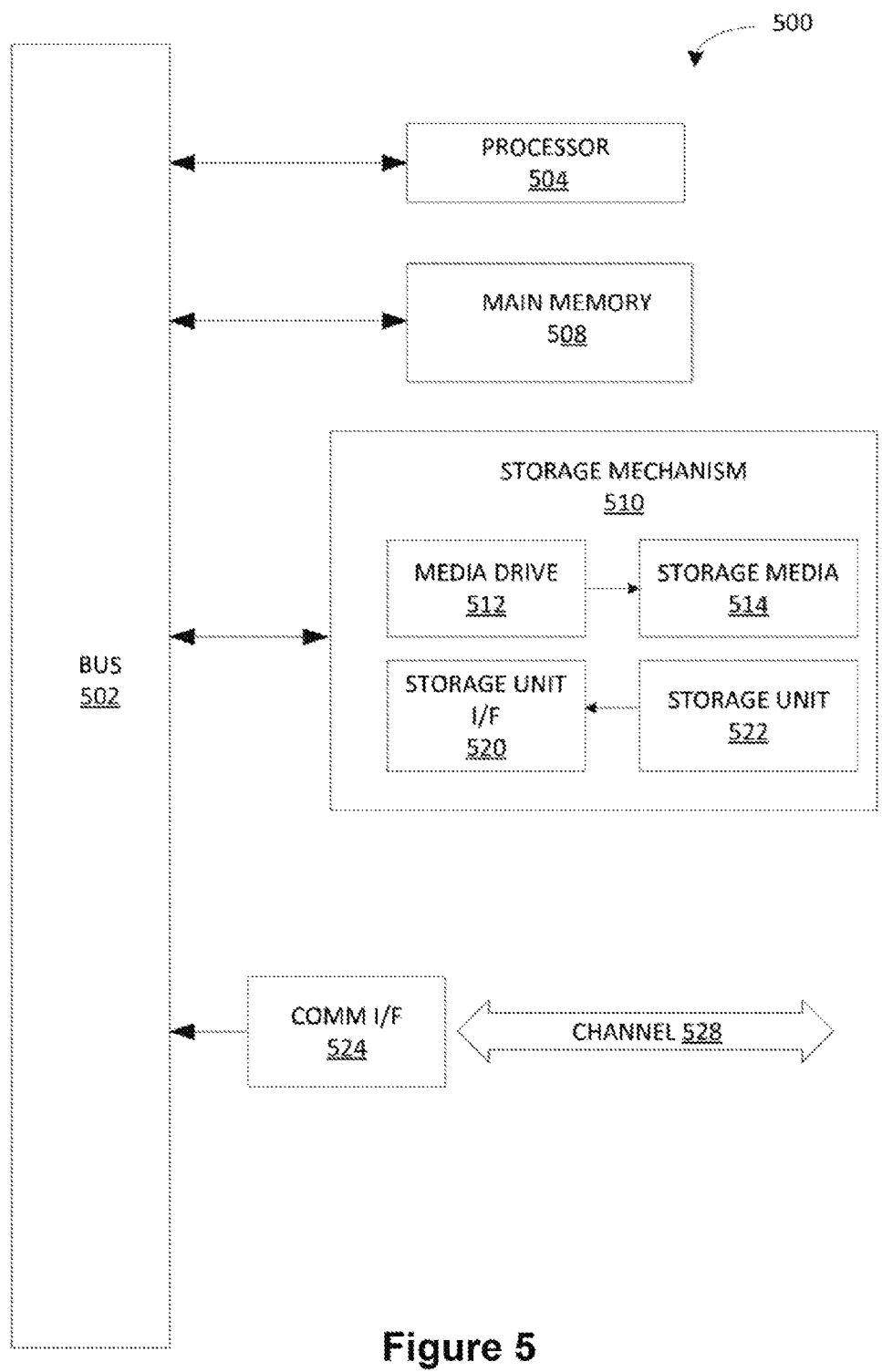
FIG. 5 illustrates an example computing module that may be used to implement various features of the systems and methods disclosed herein.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 5. Various embodiments are described in terms of this example-computing module 600. After reading this description, it will become apparent to a person skilled in the relevant art how to implement the technology using other computing modules or architectures.

Referring now to FIG. 5, computing module 500 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a floppy disk drive, a magnetic tape drive, an optical disk drive, a CD or DVD drive (R or RW), or other removable or fixed media drive might be provided. Accordingly, storage media 614 might include, for example, a hard disk, a floppy disk, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 608, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the disclosed technology as discussed herein.

Figure 6:
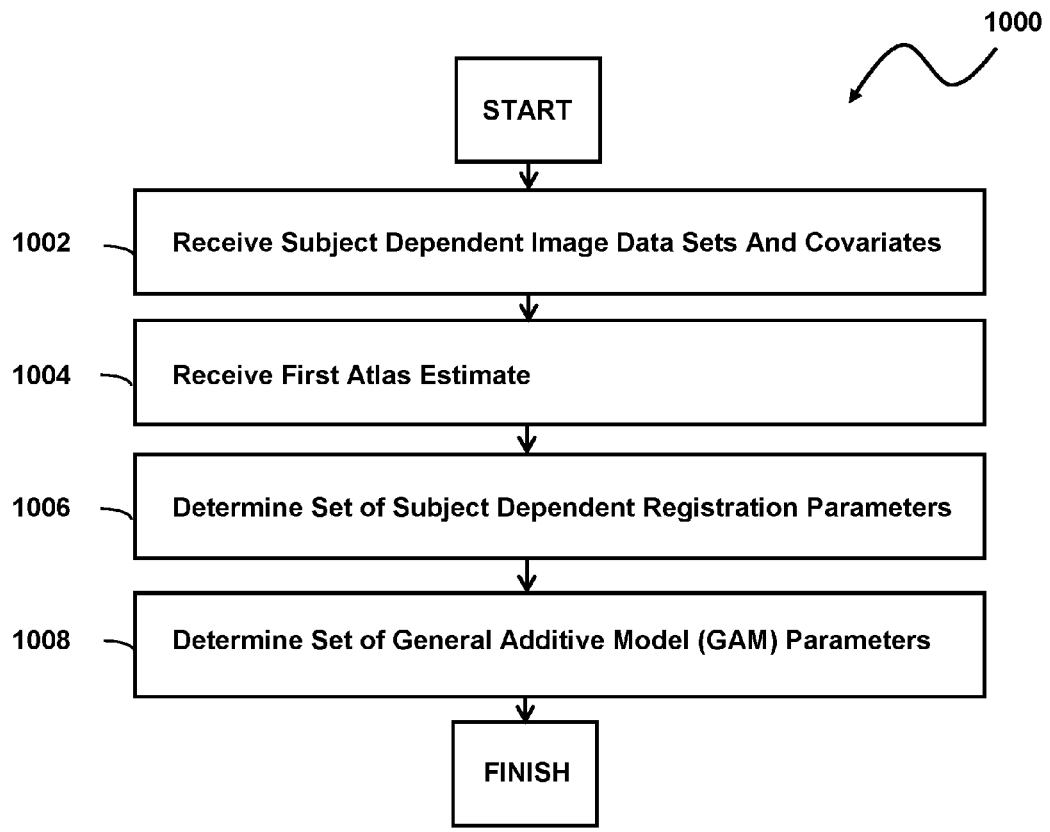
FIG. 6 illustrates a method for building an atlas.

FIG. 6 illustrates a method 1000 for building an atlas, in accordance with one or more implementations. The operations of method 1000 presented below are intended to be illustrative. In some implementations, method 1000 may be accomplished with one or more additional operations not described, and/or without one or more of the operations discussed. Additionally, the order in which the operations of method 1000 are illustrated in FIG. 6 and described below is not intended to be limiting.

In some implementations, one or more operations of method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, subject dependent image data sets and corresponding covariates may be received. The subject dependent image data sets and covariates may be received for individual ones of a plurality of subjects. The subject dependent image data sets may be related to target anatomical regions of the subjects. In some implementations, the target anatomical region is one or more of a brain, a heart, a lung, a kidney, a liver, and/or other anatomical regions. The subject dependent image data sets may be received from an image data source and/or other data sources. In some implementations, the image data source comprises an imaging modality, a picture archive communication system (PACS), and/or other sources. In some implementations, the subject dependent covariates may be received from the image data source, a demographic data source, and/or other data sources. The covariates may include demographic parameters, imaging data parameters, and/or user input. Imaging data parameters may include without limitation: mean signal strength from different imaging modalities, imaging modality parameters (for example scanner type, field strength, flip angle, acquisition properties such as TR, TE for MR modality) width, center, brightness, contrast, gamma, signal to noise ratio, field of view, plane of view for 2-D image sets (axial, coronal, sagittal), table position, target anatomy, image sequence type (T1, T2, etc.), or other image parameters that may affect the appearance of an image data set for a given anatomical structure. Demographic parameters may include without limitation: age, gender, ethnicity, genetic factors, medical history, and/or relevant clinical measures. User input can be treated as an extension of demographic parameters and may include without limitation: diagnosis, medical history data, reason for exam, clinical measures, and/or manual input to compensate for any missing or incorrect parameters. Operation 1002 may be performed by a GAM server that is the same as or similar to GAM server 120 (as described in connection with FIG. 1), in accordance with one or more implementations.

At an operation 1004, a first atlas estimate may be received. Operation 1004 may be performed by a GAM server that is the same as or similar to GAM server 120 (as described in connection with FIG. 1), in accordance with one or more implementations.

At an operation 1006, a set of subject dependent registration parameters may be determined. The subject dependent registration parameters may be determined by registering the subject dependent image data set to the first atlas estimate and/or other methods. Operation 1006 may be performed by a registration engine that is the same as or similar to registration engine 126 (as described in connection with FIG. 1), in accordance with one or more implementations.

At an operation 1008, a set of GAM parameters may be determined. The GAM parameters may be determined based on the registration parameters as a function of the covariates. Operation 308 may be performed by a GAM engine that is the same as or similar to GAM engine 122 (as described in connection with FIG. 1), in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flowcharts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

In some implementations, the present invention provides an atlas comprising values representative of magnetic resonance properties of a magnetic resonance (MR) scan and optionally, prior probability data relating to tissue type. Further embodiments of the invention involve a system including an MR scanner and the atlas for use in alignment of an MR scan, such as a localizer scan, to obtain a specific geometry of the data acquired during a subsequent scan. Also, a system includes an MR scanner and the atlas for automatic segmentation of an MR scan. Methods of making and using the atlas and system are also provided. In some implementations, the present invention generally relates to magnetic resonance and other biological scan data.

Magnetic resonance imaging is a complex interaction between protons in biological tissues, a static and alternating magnetic field (the magnet), and energy in the form of radio-frequency waves of a specific frequency (RF), introduced by coils placed next to the subject. The energy state of the hydrogen protons is transiently increased. The subsequent return to equilibrium (relaxation) of the protons results in the release of RF energy which can be measured by the same surface coils that delivered the RF pulses. The RF energy, also referred to as the RF signal or echo, is complex and is thus transformed by Fourier analysis into useful information used to form an MR image.

In some implementations, the present invention provides apparatus and methods for processing data associated with magnetic resonance (MR) scanning. In particular, in one embodiment, the present invention provides an atlas comprising at least one value representative of a magnetic property and, optionally, at least one value representative of tissue type prior probability. In a further embodiment, the present invention provides an atlas comprising a plurality of values representative of magnetic properties of a plurality of spatial locations of a plurality of subjects. In one embodiment, a system is provided having both an MR scanner and an atlas of the present invention. In a further embodiment, the invention provides methods of making and using the atlas and system.

The apparatus and methods of the present invention provide a model having data representative of one or more subjects. The data includes magnetic property values, optionally, tissue type prior probability values. The atlas can be used to automatically align an MR scan, such as a localizer scan, to obtain a specific geometry of the data acquired during a subsequent scan. The atlas may also be used to automatically identify, or segment, tissue type of a subject based on MR scan data of the subject.

According to one embodiment of the invention, an atlas is provided comprising a plurality of values representative of a magnetic property of a plurality of spatial locations of a subject as determined by magnetic resonance. According to a further embodiment, an atlas is provided comprising values representative of a statistical representation of a magnetic property of a plurality of spatial locations of a plurality of subjects. The present invention also provides a system comprising an MR scanner and an atlas. For example, the atlas may contain magnetic property data. The system can be used to automatically align an MR scan, such as a localizer scan, to obtain a specific orientation of the data acquired during a subsequent scan. The system may also be used to automatically identify, or segment, tissue type of a subject based on MR scan data of the subject.

Methods of using the atlas are further provided herein. In one embodiment, a method of using the atlas having magnetic property values to obtain a specific geometry of data to be acquired during a subsequent scan is provided. In a variation of this embodiment, a method of using the atlas may additionally involve tissue type probabilities.

Methods of using the atlas are further provided herein. In one embodiment, a method of using the atlas having magnetic property values to determine tissue type is provided. In a variation of this embodiment, a method of using the atlas may additionally involve tissue type probabilities.

According to a further embodiment of the invention, a method is provided for obtaining information about a subject having the steps of providing a magnetic resonance scanner, providing an atlas having magnetic resonance data derived from at least one other subject and processing information received from the scanner pertaining to the subject. Also included are the steps of reading the atlas and determining alignment of the magnetic resonance scan to obtain a specific geometry of a subsequent magnetic resonance scan.

According to another embodiment of the invention, another method is provided for obtaining information about a subject. This method involves the steps of providing magnetic property values corresponding to tissue types pertaining to the subject, providing an atlas having magnetic property values derived from at least one other subject, along with labeling tissue types of a tissue corresponding to the magnetic resonance property values pertaining to the subject by using the atlas having the magnetic resonance values derived from at least one other subject.

According to a further embodiment of the invention, a method is provided for creating an atlas by providing a first magnetic resonance modality volume pertaining to a subject, divided into voxels, and recording a magnetic property value in a node of the atlas corresponding to a voxel of the first magnetic resonance modality volume.

Another embodiment of the invention involves a method for creating an atlas. A first magnetic resonance modality volume is provided pertaining to a subject and divided into voxels. A labeled volume is provided indicating tissue types of tissue corresponding to the voxels. Distortion of the first magnetic resonance modality volume is corrected. Magnetic property distribution parameters are extracted for each tissue type identified at each voxel. Also, magnetic property data is recorded corresponding to each tissue type in a node of the atlas corresponding to a voxel of the first magnetic resonance modality volume.

According to another embodiment, a method for creating an atlas is provided wherein a voxel intensity is obtained from an image representative of at least one magnetic modality of a voxel of a subject, a magnetic property value is derived from the voxel intensity, and the magnetic property value is written to a node of the atlas corresponding to the voxel.

A further embodiment of the invention provides a method for processing an image of a subject. An atlas is provided having magnetic property values derived from at least one other subject. The image is aligned to the atlas, and the image is segmented into segments. The segments are labeled to designate a tissue type of a tissue corresponding to the magnetic property values pertaining to the subject by the use of the atlas. An image is thus obtained pertaining to magnetic property values of the subject.

It will further be appreciated that in the methods of the present invention, distortion may be corrected prior to entering the data into the atlas, as well as prior to processing newly acquired data in conjunction with the atlas.

The present invention, in various embodiments, involves an atlas containing values representative of magnetic properties of a magnetic resonance (MR) scan and optionally prior probability data relating to tissue type. Further embodiments of the invention involve a system including an MR scanner and the atlas for use, for example, in alignment of an MR scan and for automatic segmentation of an MR scan. Methods of creating and using the atlas and system are also provided.

As used herein, the following terms are defined as follows:

T1 and T2 relaxation times: The rate of return to equilibrium of perturbed protons is referred to as the relaxation rate. The relaxation rate is different for different normal and pathologic tissues. The relaxation rate of a hydrogen proton in a tissue is influenced by surrounding molecular environment and atomic neighbors. Two relaxation rates, the T1 and T2 relaxation times, may be measured. The T1 relaxation rate is the time for 63% of the protons to return to their normal equilibrium state, while the T2 relaxation rate is the time for 63% of the protons to become dephased owing to interactions among adjacent protons. The intensity of the signal and thus the image contrast can be modulated by altering certain parameters, such as the interval between RF pulses (TR) and the time between the RF pulse and the signal reception (TE). So-called T1-weighted (T1W) images are produced by keeping the TR and TE relatively short. Under these conditions, contrast between structures is based primarily on their T1 relaxation differences. T2-weighted (T2W) images are produced by using longer TR and TE times.

TR: The time between repetitions of RF in an imaging sequence.

TE: The time between the RF pulse and the maximum in the echo in a spin-echo sequence.

Flip Angle: The angle that the magnetic moment vector rotates when applying a B1 RF pulse field.

T1: The time to reduce the difference between the longitudinal magnetization and its equilibrium magnetization by an exponential factor.

T2: The time to reduce the transverse magnetization by an exponential factor.

PD: The concentration of spins.

T1-weighted: A magnetic resonance image where the contrast is predominantly dependent on T1.

T2-weighted: A magnetic resonance image where the contrast is predominantly dependent on T2.

PD-weighted: A magnetic resonance image where the contrast is predominantly dependent on PD.

Diffusion-weighted: A magnetic resonance image where the contrast is predominantly dependent on diffusion weighting gradient.

Magnetization Transfer-weighted: A magnetic resonance image where the contrast is predominantly dependent on magnetization transfer saturation effect.

Tissue Type: As used herein, "tissue type" can be used to designate a classification or characteristic of a tissue, such as tissue within a voxel. For example, when used with a human brain as the subject, tissue type can include, without limitation, gray matter, white matter and cerebrospinal fluid. Optionally, the tissue type can be more specific, such as referring to anatomical structure. For example, in the case of a brain as the subject, the tissue type may designate gray matter and/or, more specifically, hippocampus, or other appropriate anatomical structure label. In another example, in the case of a spine as a subject, the tissue type may designate bone, and/or more specifically vertebral bodies, or other appropriate anatomical structure labels. In yet another example, in the case of the kidney as a subject, the tissue type may designate the cortex, and/or more specifically nephrons, or other appropriate anatomical structure labels.

Localizer scan: A low-resolution scan acquired at the beginning of a scanning procedure to estimate the precision of the acquisition geometry relative to the subject to be imaged.

Subsequent scan: A high-resolution scan acquired on the basis of the localizer geometry, such as orientation, dimensions, or voxel size.

Magnetic property: A magnetic property of protons, such as T2, T1, PD, diffusion or magnetization transfer.

Figure 7:
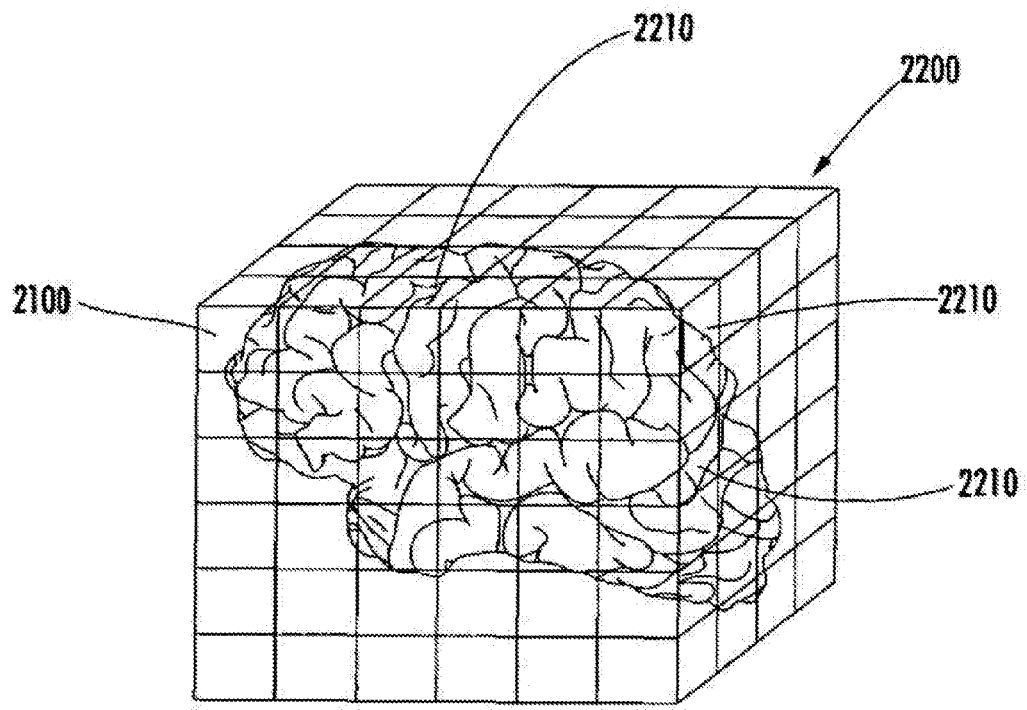
FIG. 7 provides a subject and a grid pattern illustrating voxels of a subject.

The present invention is applicable to a wide variety of MR scans of a subject including animals (e.g. mammals such as humans and other animals), as well as specific portions of a subject (e.g., organ, limb, or a portion of an organ or limb), referred to herein as the "target". In the description below, "subject" and "target" may be used interchangeably to refer to a scan area of interest. Use of the term "subject" or "target" is not intended to be limiting. Each subject/target is divided in three-dimensional space into voxels. With reference to FIG. 7, a subject/target 2100, such as a human brain, is shown with an illustrative grid pattern 2200 signifying the locations of voxels 2210. Each voxel 2210 represents a three-dimensional portion of the subject 2100. A voxel 2210 may be of various dimensions and can have different dimensions along different axes within the subject 2100.

Figure 8:
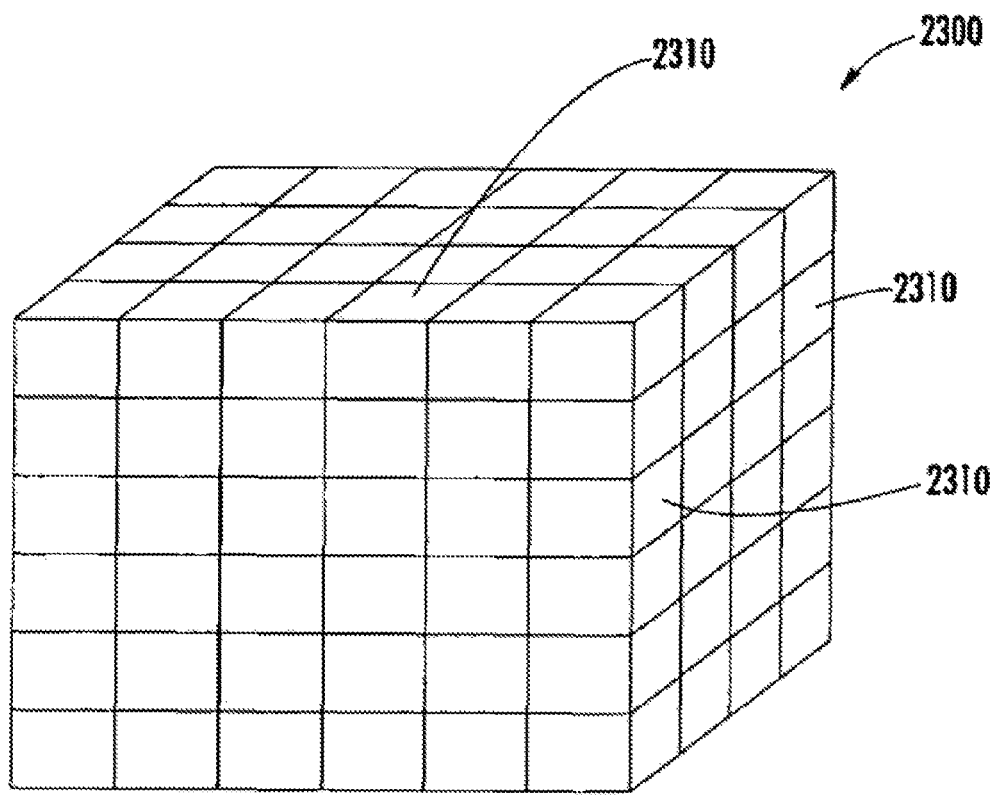
FIG. 8 illustrates an atlas.

As shown in FIG. 8, an atlas 2300 is provided according to an embodiment of the invention. While illustrated as a three-dimensional structure, the invention is not so limited, as the atlas 2300 may be formed of any of a variety of data structures as will be apparent to one of ordinary skill in the art. The atlas 2300 includes nodes 2310. According to an embodiment of the invention, each node 2310 corresponds to a voxel 2210 (of FIG. 7) representing a portion of the subject/target 2100. Alternatives of the invention may involve fewer nodes 2310 than voxels 2210. In such a case, a node 2310 may be configured to represent a plurality of voxels 2210 or the nodes 2310 may represent only a subset of the overall voxels 2210.

Figure 9:
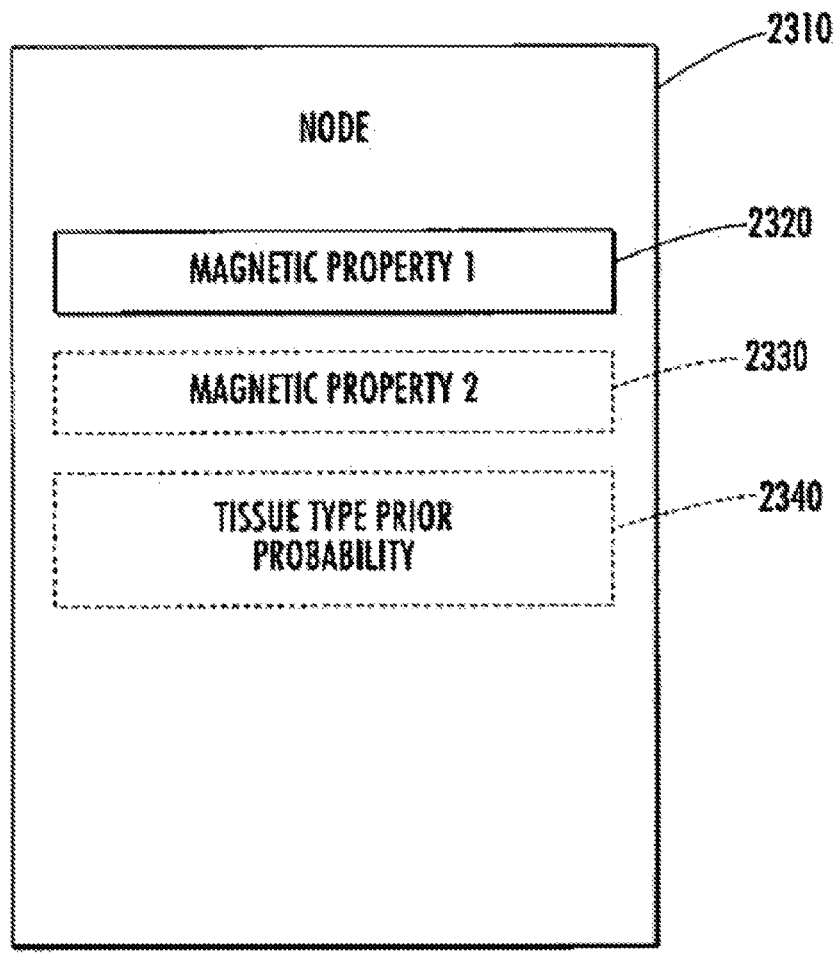
FIGS. 9-14 illustrate nodes of an atlas according to various embodiments of the invention.

FIGS. 9-14 provide various configurations of the nodes 2310 according to alternative embodiments of the invention. Each node 2310 is configured to store information relating to the corresponding voxel 2210. As shown in FIG. 9, the node 2310 may be configured to have a magnetic property 2320 corresponding to the voxel 2210. Magnetic properties may include, but are not limited to, T1, T2, proton density (PD), magnetization transfer, diffusion tensor and derived variables, such as anisotropy and diffusivity. According to one embodiment of the invention, the magnetic properties may be computed from the images, based on a forward model, and the MR acquisition parameters, including, but not limited to, TR, TE, and flip angle. Determination of such magnetic properties and details regarding the MR acquisition parameters can be found in *Magnetic Resonance Imaging, Physical Principle and Sequence Design*, E. M. Haacke et al., Wiley-Liss, 1999, pp. 637-667, which is incorporated herein by reference.

Optionally, a second magnetic property 2330 corresponding to the voxel 2210 may also be stored in the node 2310. Additional magnetic properties may also be stored in the node 2310.

A tissue type prior probability 2340 corresponding to a tissue type found in the voxel 2210 may optionally be stored in the node 2310. When used with a human brain as the subject, tissue type can include, without limitation, gray matter, white matter and cerebrospinal fluid. Optionally, the tissue type can be more specific, such as referring to anatomical structure. For example, in the case of a brain as the subject, the tissue type may designate gray matter and/or, more specifically, the hippocampus, or other appropriate anatomical structure label. In another example, in the case of the spine as a subject, the tissue type may designate bone, and/or more specifically vertebral bodies, or other appropriate anatomical structure labels. In yet another example, in the case of the kidney as a subject, the tissue type may designate the cortex, and/or more specifically nephrons, or other appropriate anatomical structure labels. It will be appreciated that the tissue type of the voxel 2210 may be determined by human labeling or may be determined by other known methods such as an algorithm (e.g. *Adaptive Segmentation of MRI Data*, Wells W M, at al., *IEEE Transactions on Medical Imaging*, 1996; 15:429-442 (corrected version available at: http://citeseer.nj.nec.com/cache/papers/cs/19782/http:zSzzSzsplweb.bwh.harvard.edu:8 0 00zSzpageszSzpplzSzswzSzpaperszSztmi-96.pdf/ wells96adaptive.pdf), *Statistical Approach to Segmentation of Single-Channel Cerebral MR Images*, Rajapakse J C, et al., *IEEE Transactions on Medical Imaging*, 1997, Vol. 16, No. 2: 176-86, and *Automated Model-Based Bias Field Correction of MR Images of the Brain*, Van Leemput, K. et al., *IEEE Transactions on Medical Imaging*, 1999, Vol. 18, No. 10), which are incorporated herein by reference.

Figure 10:
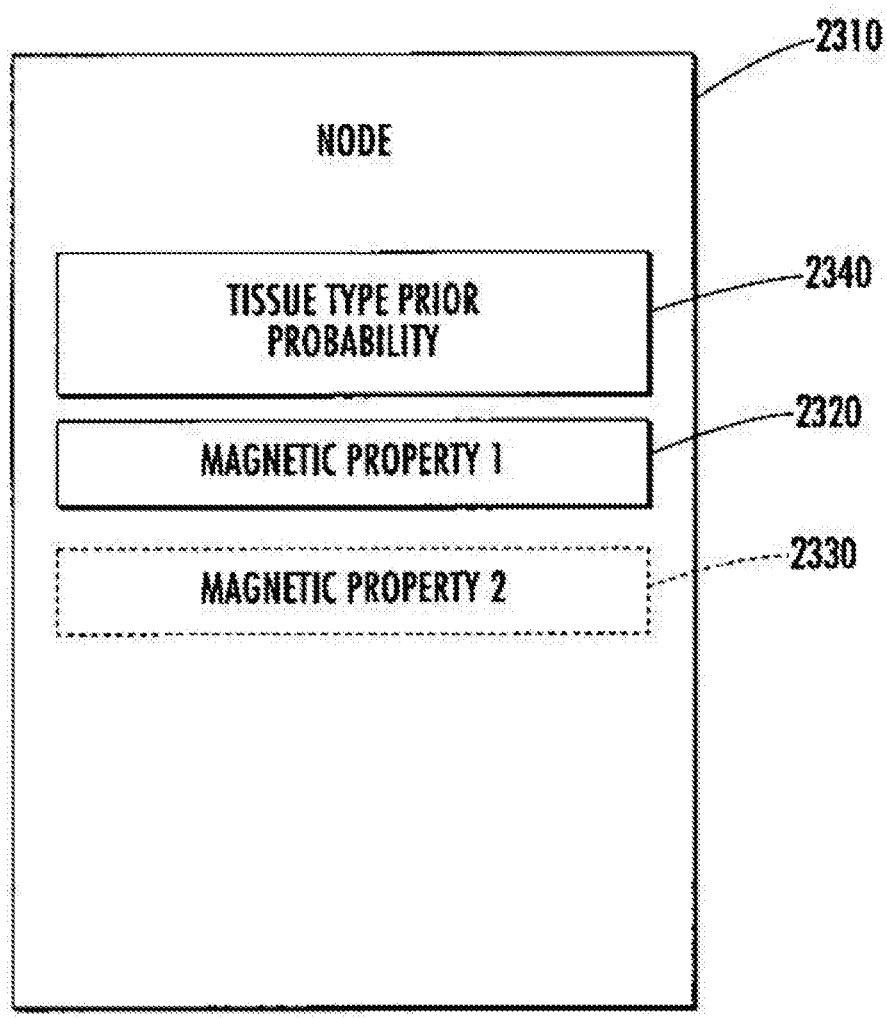

According to a further embodiment of the invention, a node 2310 may include a tissue type prior probability 2340 corresponding to a tissue type found in the voxel 2210, as illustrated in FIG. 10. According to this embodiment, a first magnetic property 2320 is also stored. Optionally, a second magnetic property 2330, or additional magnetic properties, may also be stored in the node 2310.

Figure 11:
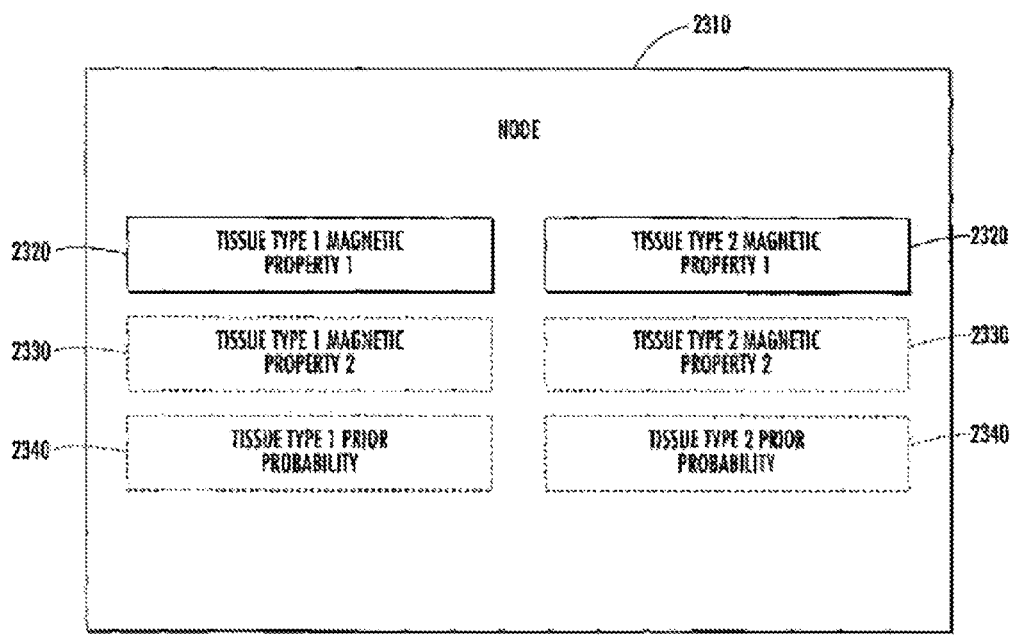

According to a further embodiment of the invention, as shown in FIG. 11, one or multiple magnetic properties may be determined for each of the tissue types located at the corresponding voxel 2210. Therefore, as shown by way of example in FIG. 11, if a voxel 2210 has two tissue types located at the voxel 2210, as determined from a plurality of subjects, one or more magnetic properties 2320, 2330 may be stored for each of the tissue types. As shown in FIG. 11, a value of a first magnetic property 2320 may be stored for the tissue type 1 at the corresponding voxel. Optionally, a value of a second magnetic property 2330 may also be stored for tissue type 1. Separate magnetic properties 2320, 2330 may also be stored for the values corresponding to the tissue of tissue type 2. This variation of the invention is useful in conjunction with an atlas 2300 formed of information from more than one subject 2100. A tissue type probability 2340 may also be optionally stored in the node 2310 for one or more of the tissue types detected at the corresponding voxel 2210.

Figure 12:
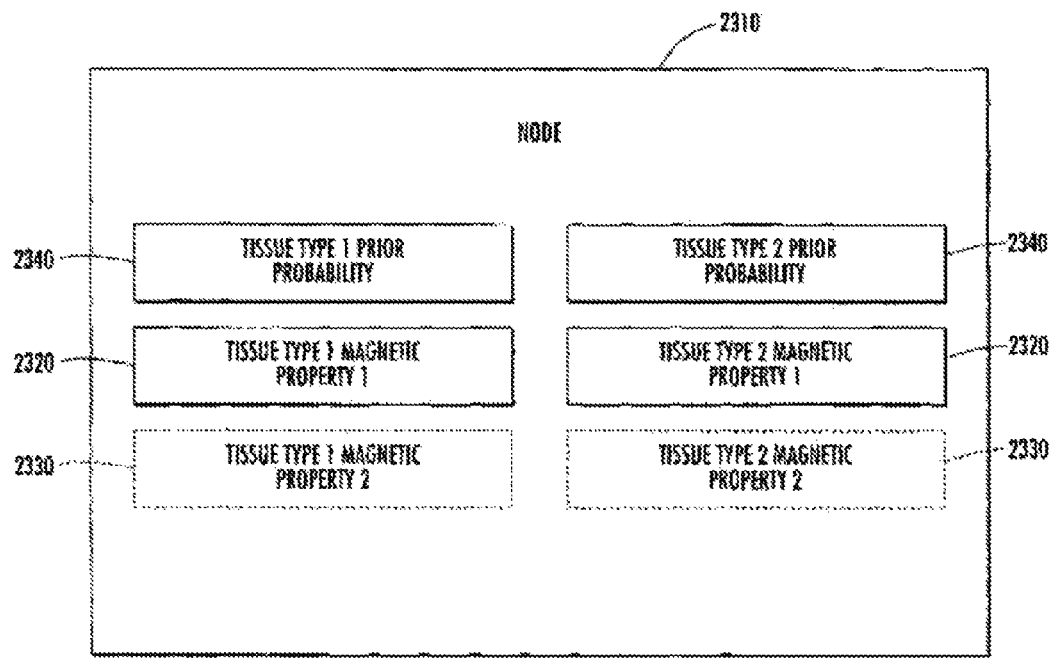

In a further embodiment, illustrated by way of example in FIG. 12, a tissue type prior probability 2340 may be stored at a node 2310 for each tissue type located at a corresponding voxel 2210. A magnetic property 2320 is also stored at the node 2310 for each tissue type. Optionally, one or more further magnetic properties 2330 may also be stored at the node 2310.

Figure 13:
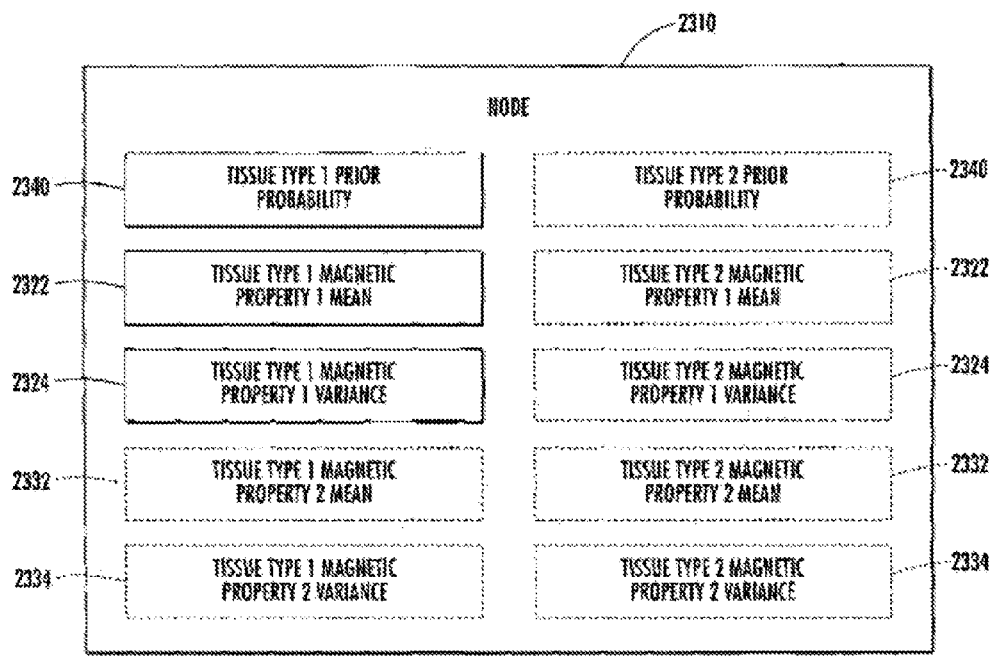

A further embodiment of a node 2310 is illustrated in FIG. 13. The node 2310 of FIG. 13 provides a tissue type prior probability 2340 and statistical data pertaining to a magnetic property of the tissue of a corresponding voxel 2210, relative to a plurality of subjects. As shown by way of example in FIG. 13, a mean 2322 of the values of a first magnetic property for a first tissue type at the corresponding voxel 2210 is provided. A variance 2324 of the values of a first magnetic property for the first tissue type at the corresponding voxel 2210 is also provided.

The node 2310 of FIG. 13 may also optionally include statistical data pertaining to one or more additional magnetic properties, such as a mean 2332 and variance 2334 of a second magnetic property.

The node 2310 of FIG. 13 is also optionally suitable for use with an atlas 2300 containing information from a plurality of subjects 2100. Any of the data 2322, 2324, 2332, 2334, 2340 as described above in relation to a first tissue type, may also be determined in relation to a second tissue type and stored.

Figure 14:
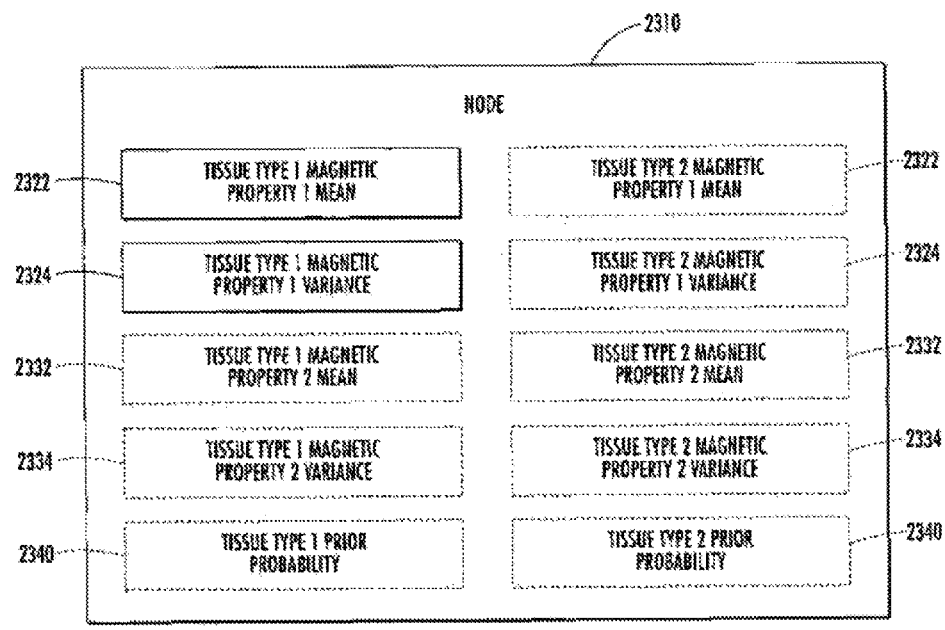

FIG. 14 illustrates a node 2310 of a further embodiment of the invention providing statistical data, such as a mean 2322 and a variance 2324, of the values of a first magnetic property for a first tissue type at a corresponding voxel 2210. Optionally, further statistical data 2332, 2334 or a tissue type prior probability 2340 may be provided. Similar information 2322, 2324, 2332, 2334, 2340 may also be optionally provided relating to further tissue types at a corresponding voxel 2210.

As illustrated by way of example in FIGS. 15A and 15B, the determination of a mean 2322 and a variance 2324 for a first magnetic property can be determined. FIG. 15A provides a table 2400 having the sample magnetic property values for an analogous voxel of each of three subjects. FIG. 15B illustrates the three steps 2410, 2420, 2430 involved in determining the content of the node 2310 corresponding to the illustrative voxel. As shown in step 1 (2410), the tissue type is 1, the mean of the value is 100 and the variance is 0. The prior probability of this node corresponding to a voxel of tissue type 1 is 1. Step 2 (2420), adds the data of the second subject to the data already tabulated from the first subject. Therefore, the mean now rises to 150, while the remaining data is unchanged, as the tissue type is 1 for both subjects, leaving the prior probability at 1.

Step 3 (2430), illustrates a node configuration illustrated in FIG. 13 or 14 by the tabulation of statistical data per tissue type for each node. Because the tissue type for the third subject is 2, a second set of statistical data is tabulated for the new tissue type, while the first set of data is updated in view of the third subject. The mean and variance of tissue type 1 remain unchanged. The prior probability of tissue type 1, however, now changes to ⅔. The mean of tissue type 2 is 50, and the variance 0. The prior probability of tissue type 2 is ⅓.

In another embodiment, additional data may be stored at each node relating to the corresponding voxel or a representation thereof. For example, image intensity data, expressed in arbitrary units, may be stored. Alternatives include those apparent to one of skill in the art.

In another embodiment, global prior probabilities may be stored in the atlas of the present invention. Global probabilities indicate the overall prior probability of something, such as a tissue type appearing in a particular area, or anywhere, in a subject. The global mean and variance of various magnetic properties may also be determined and stored for each tissue type. Such global values may be stored at a variety of locations in the atlas, such as in a header, or alternatively, at each node.

Figure 16:
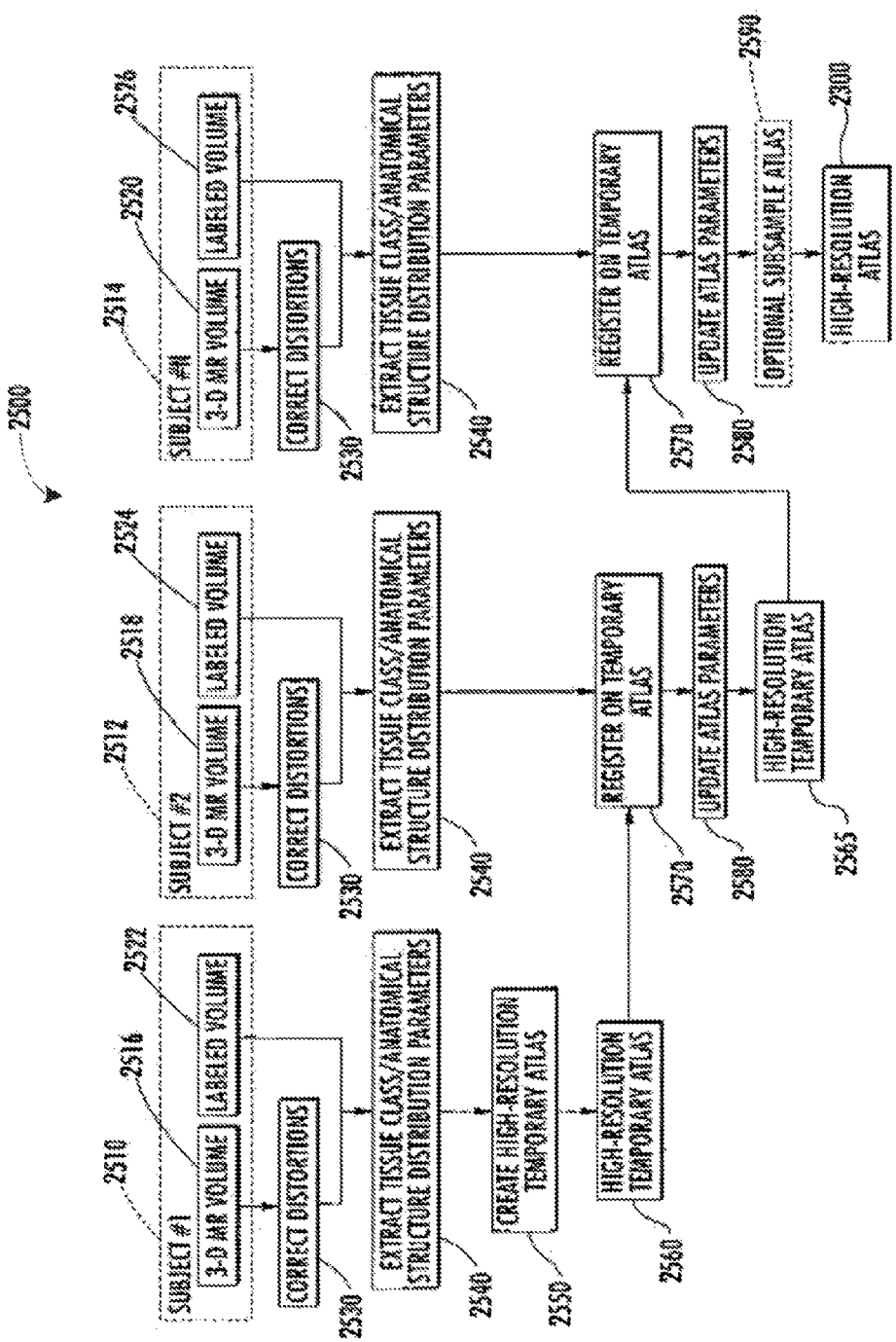
FIG. 16 provides a sample method for the creation of an atlas.

As shown by way of example in FIG. 16, a method 2500 is provided according to an embodiment of the invention for the creation of an atlas 2300. The atlas is built from one or more subject data sets 2510, 2512, 2514. A subject data set may contain at least one MR scan 2516, 2518, 2520 of a subject (e.g. an organ or a portion of an organ). The MR scans can be, but are not limited to, T1, T2, proton density (PD), magnetization transfer, diffusion tensor or derived variables such as anisotropy and diffusivity.

Distortions are then corrected in the MR scan 2516, step 2530. Corrections of distortion are known to one of ordinary skill in the art and are discussed in more detail in relation to FIG. 17 herein.

According to one embodiment, a subject's data set used in creating or adding to an atlas can also contain a labeled representation 2522, 2524, 2526 of the MR scan(s), such as a segmented volume identifying each tissue type/anatomical structure. The labeled representation can be obtained by way of manual labeling (e.g. by experienced anatomists) and/or by way of automatic segmentation methods as described by way of example in Wells, supra, *Statistical Approach to Segmentation of Single-Channel Cerebral MR Images*, Rajapakse J C, et al., IEEE Transactions on Medical Imaging, 1997, Vol. 16, No. 2: 176-86, and *Automated Model-Based Bias Field Correction of MR Images of the Brain*, Van Leemput, K. et al., IEEE Transactions on Medical Imaging, 1999, Vol. 18, No. 10, which are incorporated herein by reference.

Next, the tissue type and corresponding magnetic property statistical distribution data is extracted from the corrected subject data set 2510, step 2540.

A high-resolution temporary atlas 2560, step 2550, is then created by storing the tissue type and corresponding magnetic property statistical data of each voxel 2210 of the subject, in each corresponding node 2310 of the atlas 2300.

The high-resolution temporary atlas 2560 may then be used as the atlas 2300 if the atlas 2300 is to only have data pertaining to a single subject.

However, if additional subjects are to be added, the method 2500 continues with the subject data set 2512 of a second subject, and, optionally subject data sets 2514 of additional subjects. Correction of distortion, step 2530, and extraction of statistical data 2540 is conducted as in relation to the first subject data set 2510.

After each additional subject data set 2512, 2514 is processed, the tissue type and corresponding magnetic property statistical data of each voxel 2210 of the subject is registered, or aligned, with the existing node structure of the atlas 2300, step 2570. During registration, the data, such as tissue type and magnetic statistical data, corresponding to the voxels 2210 of the subject, is manipulated to correspond to the analogous voxels 2210 represented by the node 2310 structure of the atlas. Further details of registration, step 2570, are discussed in detail in relation to FIG. 17 herein.

Next, the additional data, such as tissue type and magnetic statistical data, is then added to the atlas 2300 by updating the atlas parameters, step 2580. As shown in FIG. 16, a high-resolution atlas 2565 is produced after the addition of two subject data sets 2510, 2512 to the atlas 2300. This high-resolution atlas 2565 may be used as an atlas 2300, or additional subject data sets 2514 may be added.

When the desired N subject data sets have been added to the atlas, the atlas may optionally be subsampled, step 2590 to create the atlas 2300. As discussed herein, alternatives of the invention may involve fewer nodes 2310 than voxels 2210. In such a case, a node 2310 may be configured to represent a plurality of voxels 2210 or the nodes 2310 may represent only a subset of the overall voxels 2210. Such a reduced resolution may also be generated by the subsampling, step 2590, by combining data from multiple voxels into one node. Also, only a portion of the voxels representing a portion of the subject may be used in the atlas 2300.

An atlas 2300 of the present invention may be customized for a specialized purpose. The atlas may have values of a statistical representation that are population-specific (e.g., related to age, sex and/or pathology), scanner-specific (e.g., related to manufacturer and/or scanner model), and/or acquisition sequence-specific (e.g., related to flash and/or inversion recovery). Acquisition sequences can include including, without limitation, at least one from the group of PD-, T2-, T1-, diffusion-, and magnetization transfer-weighted. Acquisition sequence-specific values may involve magnetic resonance sequence parameters, including, without limitation, at least one from the group of TR, TE and flip angle.

An atlas of the present invention may be oriented to various coordinate systems. One such example of a coordinate system is a Cartesian coordinate system, such as a Right Anterior Superior (RAS) coordinate system, used in orienting an image relative to a subject, or an arbitrarily determined coordinate system.

An atlas of the present invention may be created at various spatial resolutions. An atlas may further be sub-sampled to reduce the resolution and data required and time required for calculations. The resolution may also vary within an atlas, allowing greater resolution at areas of interest.

Figure 17:
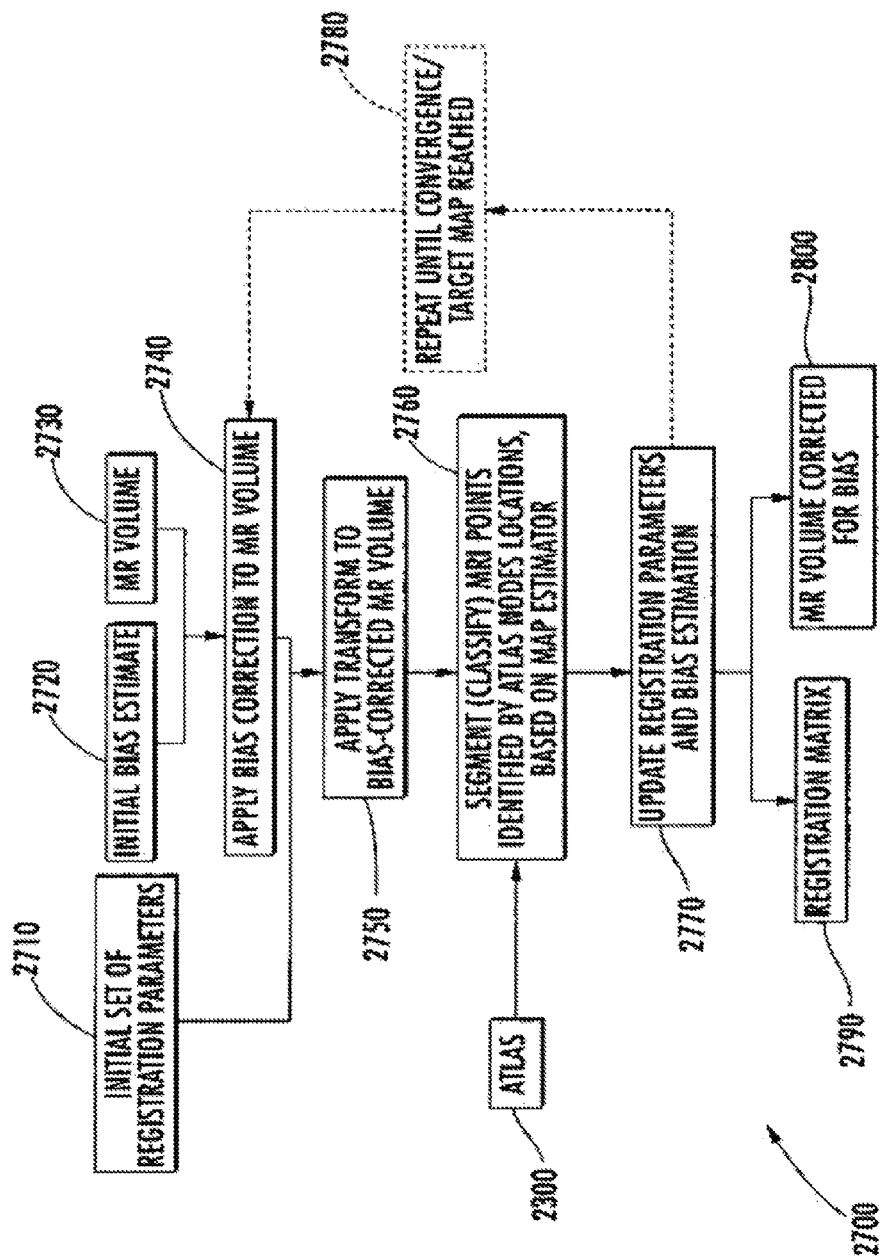
FIG. 17 provides a sample method for the registration of MR data to an atlas.

According to one embodiment of the invention, an atlas may be constructed as shown in FIGS. 16 and 17. Optionally, an atlas may be formed by data from only one subject. An atlas may be formed by N subjects, which may be determined by monitoring the change of values within the atlas upon the addition of each additional subject. According to another embodiment, when the values stored in the nodes of the atlas no longer vary within a statistical range of confidence, the addition of further subjects is no longer required.

The registration of data onto the atlas may comprise the determination of at least 6 parameters. For example, those parameters can be 3 translation shifts, 3 scaling factors and 3 rotation angles relatively to the 3 orthogonal directions of the atlas coordinate system.

Further detail regarding registration of data onto an atlas, or temporary atlas as described in FIG. 16, is illustrated by way of example in the method 2700 of FIG. 17. In FIG. 17, a method 2700 is provided according to an embodiment of the invention for the registration of MR data to an atlas 2300. The example method 2700 of FIG. 17 is also applicable to prior probability data or any other data types for association to nodes 2310 of the atlas 2300.

An initial set of registration parameters is provided, step 2710, along with an initial bias estimate, step 2720, according to methods known to one of skill in the art in relation to atlases having other types of data. See, for example, Wells, supra, *Automated Model-Based Bias Field Correction of MR Images of the Brain*, Van Leemput, K. et al., *IEEE Transactions on Medical Imaging*, 1999, Vol. 18, No. 10, and *Automatic Scan Prescription for Brain MRI*, Itti, L. et al., *Magnetic Resonance in Medicine*, 2001, Vol. 45: 486-494, which are incorporated herein by reference. The initial bias estimate of step 2720 adjusts for intensity fall-off in the portions of the image away from the image center.

A magnetic resonance (MR) volume is also provided, step 2730. The magnetic resonance volume can be generated by deriving a magnetic property value for a voxel from a voxel intensity value of a corresponding voxel of an image containing magnetic resonance data.

A bias correction is applied to the MR volume, step 2740. With regard to step 2740, and step 2530 of FIG. 16, distortion and bias can be caused by a variety of factors. For example, the distortion and bias can be subject-dependent, such as from, but not limited to, chemical shift, magnetic susceptibility, and/or per-acquisition motion. Alternatively or in addition, distortion and bias can be scanner-dependent, such as from, but not limited to, gradients non-linearity, main magnetic field non-homogeneity and/or eddy currents. Maxwell effects are a further source of potential distortion or bias.

Correction of such distortion and bias are known to one of ordinary skill in the art.

As shown in FIGS. 16 and 17, bias and distortion are corrected prior to incorporating the data into the atlas. According to a further embodiment of the invention, distortion and bias are corrected prior to processing data in conjunction with the atlas.

A transform is applied to the bias-corrected MR volume, step 2750. Linear transformations (e.g. translation, rotation, scaling) are applied to images via homogeneous matrices. According to one embodiment, they are 4×4 matrices, wherein the 3 first bottom elements always equal 0 and the last bottom elements always equals 1. Any transformation can be decomposed into a translation, a rotation and a scaling matrices. The final homogeneous matrix is then a multiplication of those 3 matrices. Details are given by way of example below: $t_x$, $t_y$ and $t_z$ being the translation parameters in the x, y and z directions, the translation homogeneous matrix is given by:

$$\begin{pmatrix} 1 & 0 & 0 & t_x \\ 0 & 1 & 0 & t_y \\ 0 & 0 & 1 & t_z \\ 0 & 0 & 0 & 1 \end{pmatrix}$$

$x_s$, $y_s$ and $z_s$ being the scaling parameters in the x, y and z directions, the scaling homogeneous matrix is given by:

$$\begin{pmatrix} x_s & 0 & 0 & 0 \\ 0 & y_s & 0 & 0 \\ 0 & 0 & z_s & 0 \\ 0 & 0 & 0 & 1 \end{pmatrix}$$

$\theta$, $\phi$ and $\varphi$ being the rotation parameters relatively to the x, y and z axis, the rotation homogeneous matrix is given by:

$$\begin{pmatrix} \cos\varphi\cos\phi + \sin\varphi\sin\theta\sin\phi & \sin\varphi\cos\theta - \cos\varphi\sin\theta\sin\phi & \cos\theta\sin\varphi & 0 \\ -\sin\varphi\cos\theta & \cos\varphi\cos\theta & \sin\theta & 0 \\ \sin\varphi\sin\theta\cos\phi - \cos\varphi\sin\theta & -\cos\varphi\sin\theta - \sin\varphi\sin\theta & \cos\theta\cos\varphi & 0 \\ 0 & 0 & 0 & 1 \end{pmatrix}$$

The voxels, or MRI points, corresponding to nodes 2310 of the atlas 2300 are segmented based on a Maximum A Posteriori (MAP) estimator, step 2760. The MAP estimator is a probability computation with statistical information stored in the atlas. The MAP estimator and its use with other types of data are known to one of ordinary skill in the art, as illustrated by way of example in Wells, supra, *Statistical Approach to Segmentation of Single-Channel Cerebral MR Images*, Rajapakse J C, et al., *IEEE Transactions on Medical Imaging*, 1997, Vol. 16, No. 2: 176-86, and *Automated Model-Based Bias Field Correction of MR Images of the Brain*, Van Leemput, K. et al., *IEEE Transactions on Medical Imaging*, 1999, Vol. 18, No. 10, which are incorporated herein by reference.

The registration parameters and bias estimation are then updated, step 2770, as is known to one of ordinary skill in the art, as illustrated by way of example in Wells, supra, *Automated Model-Based Bias Field Correction of MR Images of the Brain*, Van Leemput, K. et al., *IEEE Transactions on Medical Imaging*, 1999, Vol. 18, No. 10, and *Multimodality Image Registration by maximization of Mutual Information*, Maes, F. et al., *IEEE Transactions on Medical Imaging*, 1997, Vol. 16, No. 2, which are incorporated herein by reference. If the target MAP is not reached, the process repeats, step 2780, beginning again with application of bias correction to the MR volume, step 2740.

If the target MAP is reached, the registration matrix is provided, step 2790. The registration matrix can include sixteen (16) values, including translation parameters, scaling parameters, and a combination of the sines and cosines of rotation parameters. The registration matrix can be used to obtain a specific geometry (e.g. orientation and/or dimensions) of the data acquired during a subsequent scan, as discussed herein.

The MR volume corrected for bias is also provided, step 2800, allowing more accurate computation of the magnetic property values for each node of the atlas.

Further information regarding the details of the steps of FIG. 17 can be found in Wells, supra, *Automated Model-Based Bias Field Correction of MR Images of the Brain*, Van Leemput, K. et al., *IEEE Transactions on Medical Imaging*, 1999, Vol. 18, No. 10, and *Multimodality Image Registration by maximization of Mutual Information*, Maes, F. et al., *IEEE Transactions on Medical Imaging*, 1997, Vol. 16, No. 2, which are incorporated herein by reference.

Figure 18:
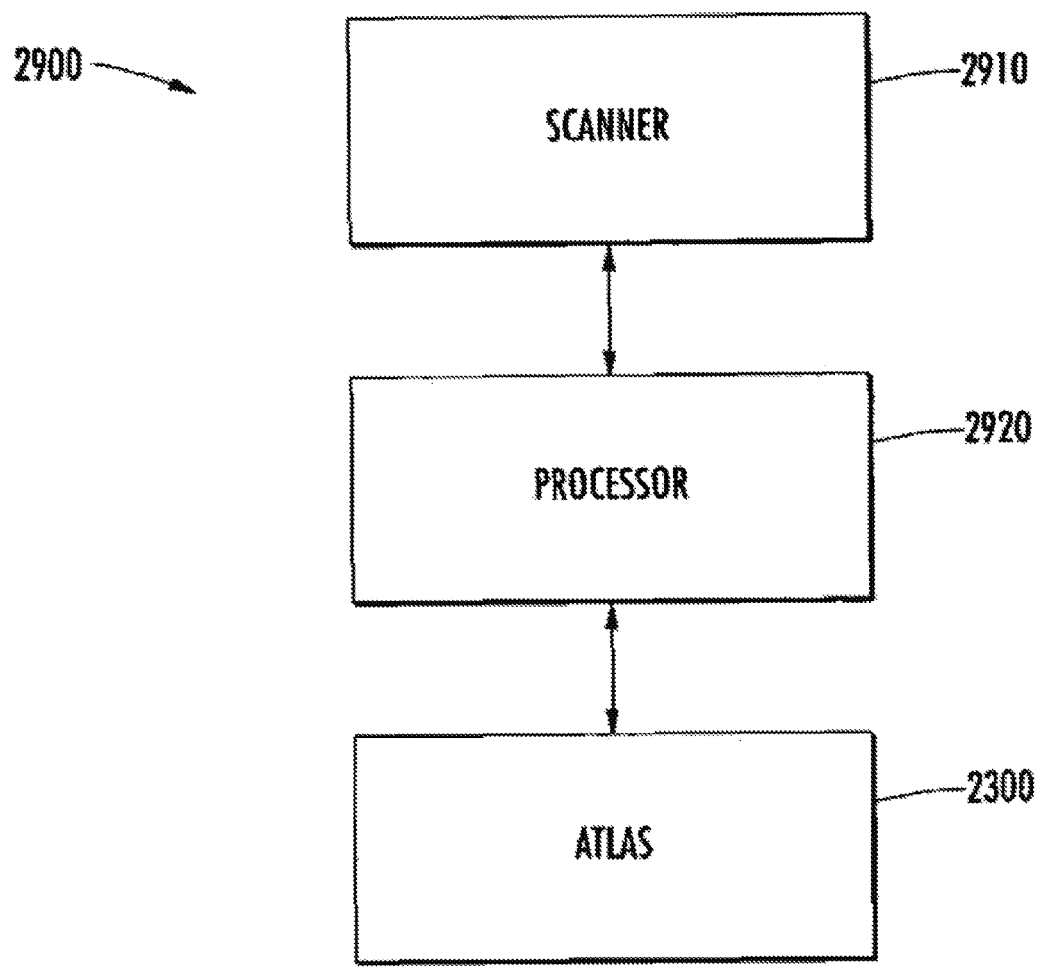
FIG. 18 provides a functional schematic of a system according to an embodiment of the invention.

According to a further embodiment of the invention, a system 2900 is provided as shown by way of example in FIG. 18. A scanner 2910 is provided to capture magnetic images. A processor 2920 is provided to interface with the scanner 2910 and the atlas 2300 in order to conduct the methods according to various embodiments of the present invention.

The atlas and system 2900 of the present invention may be used in a variety of applications. In one embodiment, a method of using the atlas with magnetic property data and optionally with tissue (or anatomical structure) type prior probabilities is provided, automatically align an MR scan, such as a localizer scan, to obtain a specific geometry of the data acquired during a subsequent scan (auto-slice prescription). Further details of this implementation can be found in U.S. Pat. No. 6,195,409, issued Feb. 27, 2001, to Chang et al., which is incorporated herein by reference.

In an additional embodiment, a method of using the atlas with magnetic property data to determine anatomical structure or detect abnormal tissue (auto-segmentation) is provided. Further details of this implementation can be found in Wells, supra, *Statistical Approach to Segmentation of Single-Channel Cerebral MR Images*, Rajapakse J C, et al., *IEEE Transactions on Medical Imaging*, 1997, Vol. 16, No. 2: 176-86, and *Automated Model-Based Bias Field Correction of MR Images of the Brain*, Van Leemput, K. et al., *IEEE Transactions on Medical Imaging*, 1999, Vol. 18, No. 10, which are incorporated herein by reference.

It will further be appreciated that in the methods of the present invention, including the applications described herein, distortion of newly obtained data may optionally be corrected prior to processing data in conjunction with the atlas. Further details of distortion correction can be found in *Sources of Distortion in Functional MRI Data*, Jezzard, P. et al., *Human Brain Mapping*, 1999, Vol. 8:80-85, which is incorporated herein by reference.

The present invention has been described by way of example, and modifications and variations of the described embodiments will suggest themselves to skilled artisans in this field without departing from the spirit of the invention. Aspects and characteristics of the above-described embodiments may be used in combination. The described embodiments are merely illustrative and should not be considered restrictive in any way. The scope of the invention is to be measured by the appended claims, rather than the preceding description, and all variations and equivalents that fall within the range of the claims are intended to be embraced therein. The contents of all references, databases, patents and published patent applications cited throughout this application are expressly incorporated herein by reference.

The invention claimed is:

1. A method for building an atlas comprising:
   receiving, for individual ones of a plurality of subjects, 1) a subject dependent image data set of a target anatomical region from an image data source, and 2) a set of subject dependent covariates from one or both of the image data source or a demographic data source;
   receiving an atlas estimate, the atlas estimate including atlas parameters;
   determining a set of subject dependent registration parameters by registering the subject dependent image data set to the atlas estimate;
   determining a set of general additive model (GAM) parameters based on the registration parameters as a function of the covariates, wherein determining the GAM parameters comprises determining a fit quality for a registration, and responsive to the fit quality for the registration falling outside a predetermined threshold range, discarding the registration parameters, or, responsive to the fit quality falling within the predetermined threshold range, using the registration parameters to determine the GAM parameters; and
   responsive to the fit quality falling within the predetermined threshold range, determining an updated atlas estimate using the GAM parameters and the atlas parameters based on a target set of covariates.

2. The method of claim 1, wherein the subject dependent covariates comprise one or both of demographic parameters or imaging parameters.

3. The method of claim 2, wherein the demographic parameters comprise one or more of age, gender, ethnicity, genetic factors, medical history, or relevant clinical measures.

4. The method of claim 2, wherein the imaging parameters comprise one or more of imaging modality parameters, manufacturer's software specifications, or manufacturer's hardware specifications.

5. The method of claim 1, wherein the atlas parameters comprise one or more of mean signal strength from different imaging modalities, scanner type, field strength, various magnetic properties for MR modality, prior probabilities of tissues and anatomic structures, prior probabilities of neighboring tissues and anatomical structures, shape parameters, or texture parameters.

6. The method of claim 1, wherein the image data source comprises one or both of an imaging modality source or a picture archive communication system (PACS).

7. The method of claim 1, further comprising:
receiving a plurality of additional subject dependent imaging data sets and corresponding additional sets of covariates,
registering the additional subject dependent imaging data sets to the atlas,
receiving additional registration parameters, and
determining additional GAM parameters as a function of the corresponding additional sets of covariates and corresponding registration parameters.

8. The method of claim 1, wherein registering the subject dependent image data set to the atlas estimate comprises an affine rigid body atlas registration process based on one or more of fiducial points, a number of voxels, voxel locations, or image intensities indicated by the image data set.

9. A system configured to build an atlas, the system comprising one or more hardware processors configured by machine-readable instructions to:
receive, for individual ones of a plurality of subjects, 1) a subject dependent image data set of a target anatomical region from an image data source, and 2) a set of subject dependent covariates from one or both of the image data source or a demographic data source;
receive an atlas estimate, the atlas estimate including atlas parameters;
determine a set of subject dependent registration parameters by registering the subject dependent image data set to the atlas estimate;
determine a set of general additive model (GAM) parameters based on the registration parameters and as a function of the covariates, wherein determining the GAM parameters comprises determining a fit quality for a registration, and responsive to the fit quality for the registration falling outside a predetermined threshold range, discarding the registration parameters, or, responsive to the fit quality falling within the predetermined threshold range, using the registration parameters to determine the GAM parameters; and
responsive to the fit quality falling within the predetermined threshold range, determine an updated atlas estimate using the GAM parameters and the atlas parameters based on a target set of covariates.

10. The system of claim 9, wherein the subject dependent covariates comprise one or both of demographic parameters or imaging parameters.

11. The system of claim 10, wherein the demographic parameters comprise one or more of age, gender, ethnicity, genetic factors, medical history, or relevant clinical measures.

12. The system of claim 10, wherein the imaging parameters comprise one or more of imaging modality parameters, manufacturer's software specifications, or manufacturer's hardware specifications.

13. The system of claim 9, wherein the atlas parameters comprise one or more of mean signal strength from different imaging modalities, scanner type, field strength, various magnetic properties for MR modality, prior probabilities of tissues and anatomic structures, prior probabilities of neighboring tissues and anatomical structures, shape parameters, or texture parameters.

14. The system of claim 9, wherein the image data source comprises one or more of an imaging modality source or a picture archive communication system (PACS).

15. The system of claim 9, wherein the one or more hardware processors are further configured to:
receive a plurality of additional subject dependent imaging data sets and corresponding additional sets of covariates;
register the plurality of additional subject dependent imaging data sets to the atlas;
receive additional registration parameters;
determine additional GAM parameters as a function of the additional corresponding sets of covariates and corresponding registration parameters; and
determine the updated atlas estimate using the additional GAM parameters and the atlas parameters based on the target set of covariates.

16. The system of claim 9, wherein the one or more hardware processors comprise a GAM server, the GAM server comprising a registration engine and a GAM engine, wherein:
the GAM server is configured to receive, for the individual ones of the plurality of subjects, the subject dependent image data set of the target anatomical region from the image data source and the set of subject dependent covariates from one or both of the image data source or the demographic data source;
the GAM server is configured to receive the atlas estimate;
the registration engine is configured to determine the set of subject dependent registration parameters by registering the subject dependent image data set to the atlas estimate;
the GAM engine is configured to determine the set of GAM parameters based on the registration parameters as a function of the covariates; and
the GAM server is configured to determine the updated atlas estimate using the GAM parameters and the atlas parameters based on the target set of covariates.

17. The system of claim 16, wherein the GAM server further comprises a prediction engine configured to determine the updated atlas based on the subject dependent covariates, the atlas estimate, the registration parameters, and the GAM parameters.

18. The system of claim 9, wherein the one or more hardware processors are configured such that registering the subject dependent image data set to the atlas estimate comprises an affine rigid body atlas registration process based on one or more of fiducial points, a number of voxels, voxel locations, or image intensities indicated by the image data set.

* * * * *